US009987315B2

(12) United States Patent
McFadden et al.

(10) Patent No.: US 9,987,315 B2
(45) Date of Patent: Jun. 5, 2018

(54) USE OF A COMBINATION OF MYXOMA VIRUS AND RAPAMYCIN FOR THERAPEUTIC TREATMENT

(71) Applicant: The University of Western Ontario, London (CA)

(72) Inventors: Grant McFadden, Gainesville, FL (US); John Barrett, London (CA); Marianne Stanford, Ottawa (CA)

(73) Assignee: The University of Western Ontario, London (CA)

( * ) Notice: Subject to any disclaimer, the term of this patent is extended or adjusted under 35 U.S.C. 154(b) by 44 days.

(21) Appl. No.: 14/049,737

(22) Filed: Oct. 9, 2013

(65) Prior Publication Data

US 2014/0134134 A1 May 15, 2014

Related U.S. Application Data

(63) Continuation of application No. 13/679,096, filed on Nov. 16, 2012, now abandoned, which is a continuation of application No. 12/850,599, filed on Aug. 4, 2010, now abandoned, which is a continuation of application No. 11/908,076, filed as application No. PCT/CA2006/000315 on Mar. 6, 2006, now abandoned.

(60) Provisional application No. 60/658,816, filed on Mar. 7, 2005.

(51) Int. Cl.
*A61K 35/768* (2015.01)
*A61K 31/436* (2006.01)

(52) U.S. Cl.
CPC .......... *A61K 35/768* (2013.01); *A61K 31/436* (2013.01); *C12N 2710/24032* (2013.01)

(58) Field of Classification Search
CPC .............. A61K 35/768; A61K 2300/00; A61K 31/436; A61K 48/00; C12N 2710/24032; C12N 2710/14143; C12N 2710/24022; C12N 2740/13043; A01K 2217/05; C07K 14/005
See application file for complete search history.

(56) References Cited

U.S. PATENT DOCUMENTS

| | | | | |
|---|---|---|---|---|
| 4,401,653 | A | 8/1983 | Eng | |
| 6,264,940 | B1 * | 7/2001 | Gromeier | C12N 15/86 424/93.2 |
| 6,596,268 | B1 * | 7/2003 | Coffey et al. | 424/93.2 |
| 7,582,614 | B2 * | 9/2009 | McFadden et al. | 514/44 R |
| 2004/0082529 | A1 * | 4/2004 | Hochberg et al. | 514/44 |
| 2004/0147541 | A1 | 7/2004 | Lane et al. | |
| 2006/0099224 | A1 * | 5/2006 | Kirn | A61K 45/06 424/199.1 |
| 2009/0035276 | A1 | 2/2009 | McFadden et al. | |
| 2009/0317362 | A1 | 12/2009 | McFadden et al. | |
| 2011/0195050 | A1 | 8/2011 | McFadden et al. | |
| 2013/0171106 | A1 | 7/2013 | McFadden et al. | |

FOREIGN PATENT DOCUMENTS

| | | | |
|---|---|---|---|
| CA | 2517147 | | 9/2004 |
| JP | 57-159716 | | 10/1982 |
| JP | 2003-514024 | | 4/2003 |
| JP | 2005-505549 | | 2/2005 |
| WO | WO 1999/018799 | | 4/1999 |
| WO | WO 2001/004318 | | 1/2001 |
| WO | WO 2001/035970 | | 5/2001 |
| WO | WO 2001/087324 | | 11/2001 |
| WO | WO 2003/020266 | | 3/2003 |
| WO | WO/2004/078206 | * | 9/2004 |
| WO | WO 2004/093854 | | 11/2004 |
| WO | WO 2005/002607 | | 1/2005 |
| WO | WO 2005/113018 | | 12/2005 |

OTHER PUBLICATIONS

McCabe et al. Vaccine 2002;20:2454-62.*
McFadden, Nat Reviews Microbiol 2005; 3:201-13.*
Liu et al J Virol 2011 ;85:3270-82.*
Kunz-Schughart et al. Journal of Biomolecular Screening, 2004, 9:273-285.*
Barrett et al (J. NeuroVirol 2007;13(6):549-60.*
Kelland et al European Journal of Cancer, 2004, 40, 827-836.*
Kerbel et al Cancer Biology & Therapy 2: 4 suppl. 1, S134-139.*
Lu et al Cancer Gene Ther. Jan.-Feb. 1999; 6(1): 64-72.*
Soudais, et al FASEB J., 2004, 18(2): 391-3.*
Barrett et al Fourteenth International Poxvirus and Iridovirus Conference, Lake Placid, NY, Sep. 2002.*
Stojdl et al Nature Med. 2000, 821-825).*
Bell et al (Cancer Cell, 2003, 4, 7-11.*
Chan et al (British Journal of Cancer, 2004, 91, 1420-1424.*
Belsham et al Virology Journal 2010, 7:7, 1-10.*
Sypula Gene Ther Mol Biol vol. 8, 103-114, 2004.*
Rapamycin | C51H79NO13—PubChem1-49, p. 1 only.*
Mossman et al Journal of Virology, 4394-4410 (Year: 1996).*
U.S. Appl. No. 13/679,096, filed Nov. 16, 2012, 2013-0171106.
U.S. Appl. No. 12/850,599, filed Aug. 4, 2010, 2011-0195050.
U.S. Appl. No. 11/908,076, filed Aug. 13, 2008, 2009-0035276.
EP 06705269.6, May 7, 2009, Extended European Search Report.
EP 11174887.7, Apr. 3, 2012, Extended European Search Report.
PCT/CA2006/000315, Jun. 29, 2006, International Search Report and Written Opinion.
PCT/CA2006/000315, Sep. 11, 2007, International Preliminary Report on Patentability.

(Continued)

*Primary Examiner* — Anoop K Singh
(74) *Attorney, Agent, or Firm* — Wolf, Greenfield & Sacks, P.C.

(57) ABSTRACT

The present invention relates to therapeutic use of a combination of Myxoma virus, including in combination with rapamycin. Treatment with rapamycin enhances the ability of Myxoma virus to selectively infect cells that have a deficient innate anti-viral response, including cells that are not responsive to interferon. The combination of rapamycin and Myxoma virus can be used to treat diseases characterized by the presence of such cells, including cancer. The invention also relates to therapeutic use of Myxoma virus that does not express functional M135R.

12 Claims, 41 Drawing Sheets

(56) References Cited

OTHER PUBLICATIONS

Barrett et al, M135R is a novel cell surface virulence factor of myxoma virus. J Virol. Jan. 2007;81(1):106-14. Epub Oct. 25, 2006.
Barrett et al., Immunomodulatory proteins of myxoma virus. Semin Immunol. Feb. 2001;13(1):73-84.
Barrett et al., MyXoma virus recombinants with improved potential as oncolytic agents. Poster presented at Oncolytic Viruses as Cancer Therapeutics Meeting in Banff, Ontario, Mar. 9-13, 2005.
Bell, Replicating oncolytic virus therapeutics—Third International Meeting. IDrugs. May 2005;8(5):360-3.
Belsham et al., Detection of myxoma viruses encoding a defective M135R gene from clinical cases of myxomatosis; possible implications for the role of the M135R protein as a virulence factor. Virol J. Jan. 16, 2010;7:7. doi: 10.1186/1743-422X-7-7.
Beretta et al., Rapamycin stimulates viral protein synthesis and augments the shutoff of host protein synthesis upon picornavirus infection. J Virol. Dec. 1996;70(12):8993-6.
Cameron et al., The complete DNA sequence of myxoma virus. Virology. Nov. 25, 1999;264(2):298-318.
Dalton et al., Molecular characterisation of virulence graded field isolates of myxoma virus. Virol J. Feb. 26, 2010;7:49. doi: 10.1186/1743-422X-7-49.
Homicsko et al., RAD001 (everolimus) improves the efficacy of replicating adenoviruses that target colon cancer. Cancer Res. Aug. 1, 2005;65(15):6882-90.
Johnston et al., A poxvirus-encoded pyrin domain protein interacts with ASC-1 to inhibit host inflammatory and apoptotic responses to infection. Immunity. Dec. 2005;23(6):587-98.
Johnston et al., High frequency of syncytium-inducing and CXCR4-tropic viruses among human immunodeficiency virus type 1 subtype C-infected patients receiving antiretroviral treatment. J Virol. Jul. 2003;77(13):7682-8.
Johnston et al., Role of the serine-threonine kinase PAK-1 in myxoma virus replication. J Virol. May 2003;77(10):5877-88.
Kerr et al., Immune responses to myxoma virus. Viral Immunol. 2002;15(2):229-46. Review.
Kuhn et al., Beta-lactams and their potential use as novel anticancer chemotherapeutics drugs. Front Biosci. Sep. 1, 2004;9:2605-17. Review.
Lalani et al., Role of the myxoma virus soluble CC-chemokine inhibitor glycoprotein, M-T1, during myxoma virus pathogenesis. Virology. Apr. 10, 1999;256(2):233-45.
Luan et al., Rapamycin blocks tumor progression: unlinking immunosuppression from antitumor efficacy. Transplantation. May 27, 2002;73(10):1565-72.
Lun et al., Myxoma virus is a novel oncolytic virus with significant antitumor activity against experimental human gliomas. Cancer Res. Nov. 1, 2005;65(21):9982-90.
Lun et al., Myxoma virus virotherapy for glioma in immunocompetent animal models: optimizing administration routes and synergy with rapamycin. Cancer Res. Jan. 15, 2010;70(2):598-608. doi: 10.1158/0008-5472.CAN-09-1510. Epub Jan. 12, 2010.
Lun et al., Targeting human medulloblastoma: oncolytic virotherapy with myxoma virus is enhanced by rapamycin. Cancer Res. Sep. 15, 2007;67(18):8818-27.
Morales et al., Genome comparison of a nonpathogenic myxoma virus field strain with its ancestor, the virulent Lausanne strain. J Virol. Mar. 2009;83(5):2397-403. doi: 10.1128/JVI.02189-08. Epub Dec. 17, 2008.
Mossman et al., Disruption of M-T5, a novel myxoma virus gene member of poxvirus host range superfamily, results in dramatic attenuation of myxomatosis in infected European rabbits. J Virol. Jul. 1996;70(7):4394-410.
Newton, Molecular neuro-oncology and development of targeted therapeutic strategies for brain tumors. Part 2: PI3K/Akt/PTEN, mTOR, SHH/PTCH and angiogenesis. Expert Rev Anticancer Ther. Feb. 2004;4(1):105-28. Review.
Oliere et al., Vesicular stomatitis virus oncolysis of T lymphocytes requires cell cycle entry and translation initiation. J Virol. Jun. 2008;82(12):5735-49. doi: 10.1128/JVI.02601-07. Epub Apr. 16, 2008.
Ponticelli, The pleiotropic effects of mTor inhibitors. J Nephrol. Nov.-Dec. 2004;17(6):762-8. Review.
Rahman et al., Oncolytic viral purging of leukemic hematopoietic stem and progenitor cells with Myxoma virus. Cytokine Growth Factor Rev. Apr.-Jun. 2010;21(2-3):169-75. doi: 10.1016/j.cytogfr.2010.02.010. Epub Mar. 7, 2010. Review.
Stanford et al., Myxoma virus oncolysis of primary and metastatic B16F10 mouse tumors in vivo. Mol Ther. Jan. 2008;16(1):52-9. Epub Nov. 13, 2007.
Stanford et al., Oncolytic virotherapy synergism with signaling inhibitors: Rapamycin increases myxoma virus tropism for human tumor cells. J Virol. Feb. 2007;81(3):1251-60. Epub Nov. 15, 2006.
Stanford et al., Rapamycin enhances myXoma virus replication in human tumor cells. Southern Ontario Gene Therapy Meeting in Ontario on Apr. 17-18, 2005. (Poster presentation).
Stanford et al., Rapamycin enhances myXoma virus replication in human tumor cells. Oncolytic Viruses as Cancer Therapeutics meeting in Banff, Alberta, Canada, Mar. 9-12, 2005. (Abstract).
Stanford et al., Rapamycin enhances myXoma virus replication in human tumor cells. Oncolytic Viruses as Cancer Therapeutics meeting in Banff, Alberta, Canada, Mar. 9-12, 2005. (Slides from oral presentation).
Stanford et al., Rapamycin enhances myXoma virus replication in human tumor cells. American Society for Virology meeting in Pennsylvania State University, Jun. 18-22, 2005. (Slides from oral presentation).
Stojdl et al., VSV strains with defects in their ability to shutdown innate immunity are potent systemic anti-cancer agents. Cancer Cell. Oct. 2003;4(4):263-75.
Sypula et al., Myxoma virus tropism in human tumor cells. Gene Thera and Mol Biol. 2004; 8:103-14.
Toda et al., Herpes simplex virus as an in situ cancer vaccine for the induction of specific anti-tumor immunity. Hum Gene Ther. Feb. 10, 1999;10(3):385-93.
Wang et al., Myxoma virus selectively disrupts type I interferon signaling in primary human fibroblasts by blocking the activation of the Janus kinase Tyk2. Virology. Apr. 25, 2009;387(1):136-46. doi: 10.1016/j.virol.2009.02.013. Epub Feb. 28, 2009.
Wu et al., Oncolytic efficacy of recombinant vesicular stomatitis virus and myxoma virus in experimental models of rhabdoid tumors. Clin Cancer Res. Feb. 15, 2008;14(4):1218-27. doi: 10.1158/1078-0432.CCR-07-1330.

* cited by examiner

Nonpermissive    Anti-IFNα/β      Anti-IFNα/β      Anti-IFNγ
WT MEFs          (200 U/ml)       (2000 U/ml)      (200,000
U/ml)

Mock Neutralization

Anti-IFNα/β
(2000 u/ml)

Daoy D384

USE OF A COMBINATION OF MYXOMA VIRUS AND RAPAMYCIN FOR THERAPEUTIC TREATMENT

CROSS-REFERENCE TO RELATED APPLICATION

This application is a continuation of U.S. patent application Ser. No. 13/679,096, filed on Nov. 16, 2012 which is a continuation of U.S. patent application Ser. No. 12/850,599 filed Aug. 4, 2010, which is a continuation of U.S. patent application Ser. No. 11/908,076, filed Sep. 7, 2007, which is a § 371 of PCT/CA06/00315, filed Mar. 6, 2006, which claims the benefit of U.S. Provisional Application No. 60/658,816, filed Mar. 7, 2005, the disclosures of which are incorporated hereby reference in their entireties.

FIELD OF THE INVENTION

The present invention relates generally to therapeutic use of Myxoma virus and rapamycin.

BACKGROUND OF THE INVENTION

Current treatments used to treat various types of cancer tend to work by poisoning or killing the cancerous cell. Unfortunately, treatments that are toxic to cancer cells typically tend to be toxic to healthy cells as well. Moreover, the heterogenous nature of tumours is one of the primary reasons that effective treatments for cancer remain elusive. Current mainstream therapies such as chemotherapy and radiotherapy tend to be used within a narrow therapeutic window of toxicity. These types of therapies are considered blunt tools that have limited applicability due to the varying types of tumour cells and the limited window in which these treatments can be administered.

Modern anticancer therapies currently being developed attempt to selectively target tumour cells while being less toxic to healthy cells, thereby being more likely to leave healthy cells unaffected.

Oncolytic viral therapy is one approach that aims to exploit cellular differences between tumour cells and normal cells. This therapy uses replication-competent, tumour-selective viral vectors as anti-cancer agents. The oncolytic virus either specifically targets cancer cells for infection, or is more suited for efficient replication in cancer cells versus healthy cells. These replication-competent, oncolytic viruses are either naturally occurring or genetically engineered to be a highly selective and highly potent means of targeting the heterogeneous tumour population. Since the replication selective oncolytic virus does not replicate efficiently in normal cells, toxicity to the patient should be low, particularly in comparison to traditional therapies such as radiation or chemotherapy.

Numerous studies have reported oncolytic activity for various virus strains, with the most promising oncolytic viruses being a naturally occurring or genetically modified version of adenovirus, herpes simplex virus 1 ("HSV1"), Reovirus, Vaccinia Virus, Vesicular Stomatitis Virus ("VSV") or Poliovirus. Modified oncolytic viruses currently under investigation as anticancer agents include HSV, adenovirus, Newcastle disease virus ("NDV"), Reovirus and Vaccinia virus, measles, VSV and poliovirus. Various oncolytic viruses are in Phase I and Phase II clinical trials with some showing sustained efficacy. However, it is unknown which viruses will best fulfill the oncolytic goals of sustained replication, specificity and potent lytic activity. A completely efficient candidate, for an oncolytic viral vector would be one that has a short lifecycle, forms mature virions quickly, spreads efficiently from cell to cell and has a large genome ready for insertions. As well, evidence suggests that inhibiting the early innate immune response and slowing the development of Th1 responses are important for the efficacy of oncolytic therapy. It is clear that human viruses are highly immunogenic, as measured by the high level of antibody and T cell responses that are observed in the normal population for many of the viruses being considered for the development of oncolytic viruses.

Clinical work has shown that current oncolytic viruses are indeed safe, but are not potent enough as monotherapies to be completely clinically effective. As insufficient or inefficient infection of tumour cells is usually observed, the current movement is to arm candidate viruses by genetically engineering them to express therapeutic transgenes to increase their efficiency. Most of the above-mentioned oncolytic viruses are also being tested in combination with other common oncolytic therapies.

Adenovirus can be easily genetically manipulated and has well-known associated viral protein function. In addition, it is associated with a fairly mild disease. The ONYX-015 human adenovirus (Onyx Pharmaceuticals Inc.) is one of the most extensively tested oncolytic viruses that has been optimized for clinical use. It is believed to replicate preferentially in p53-negative tumours and shows potential in clinical trials with head and neck cancer patients. However, reports show that ONYX-015 has only produced an objective clinical response in 14% of treated patients (Nemunaitis J, Khuri F, Ganly I, Arseneau J, Posner M, Vokes E, Kuhn J, McCarty T, Landers S, Blackburn A, Romel L, Randlev B, Kaye S, Kirn D. *J. Clin. Oncol.* 2001 Jan. 15; 19(2):289-98).

WO96/03997 and WO97/26904 describe a mutant oncolytic HSV that inhibits tumour cell growth and is specific to neuronal cells. Further advantages are that the HSV can be genetically modified with ease, and drugs exist to shut off any unwanted viral replication. However, the application of such a common human pathogen is limited, as it is likely that the general population has been exposed and acquired an immune response to this virus, which would attenuate the lytic effect of the virus. HSV can also cause serious side effects or a potentially fatal disease.

Reovirus type III is associated with relatively mild diseases and its viral gene function is fairly well understood. Reovirus type III is currently being developed by Oncolytic Biotech as a cancer therapeutic which exhibits enhanced replication properties in cells expressing mutant ras oncogen and preferentially grows in PKR−/− cells (Strong J. E. and P. W. Lee, *J. Virology*, 1996. 70:612-616). However, Reovirus is difficult to genetically manipulate and its viral replication cannot be easily shut off.

VSV is associated with relatively mild diseases and also has well-known viral gene function. WO99/04026 discloses the use of VSV as a vector in gene therapy for the expression of wide treatment of a variety of disorders. However, VSV suffers from the same problems as the Reovirus in that it is difficult to genetically manipulate and its viral replication cannot be easily shut off.

Vaccina virus and Poliovirus are other candidate oncolytic viruses described in the art but have been associated with a serious or potentially fatal disease.

U.S. Pat. No. 4,806,347 discloses the use of gamma interferon and a fragment of IFNγ against human tumour cells. WO99/18799 discloses a method of treating disease in a mammal in which the diseased cells have defects in an interferon-mediated antiviral response, comprising administering to the mammal a therapeutically effective amount of an interferon-sensitive, replication competent clonal virus. It specifically discloses that VSV particles have toxic activity against tumour cells but that alleviation of cytotoxicity in normal cells by VSV occurs in the presence of interferon. WO99/18799 also discloses that NDV-induced sensitivity was observed with the interferon-treated tumour cells but that adding interferon to normal cells makes these cells resistant to NDV. This method aims to make cells sensitive to interferon by infecting them with interferon sensitive viruses.

SUMMARY OF THE INVENTION

The present invention is based on the unexpected discovery that rabbit Myxoma virus, including a novel Myxoma virus that does not express functional M135R protein, can selectively infect cells, including human tumour cells, that have a deficient innate anti-viral response, including those that are non-responsive to interferon, and that such infection is enhanced by treating such cells with the drug rapamycin. The term "innate" as used in this context describes non-antigen specific immune response. Since Myxoma virus does not replicate efficiently in normal human cells, the virus can therefore be used as a treatment for various disorders and conditions characterized by cells that have a deficient innate anti-viral response, including cells that are non-responsive to interferon, for example, as an oncolytic treatment for cancer. The virus can also be used to identify cells that have a deficient innate anti-viral response and to image these cells in vivo.

In one aspect, the present invention provides a method for inhibiting a cell that has a deficient innate anti-viral response comprising administering to the cell an effective amount of a combination of Myxoma virus and rapamycin.

In one aspect, the invention provides a method for treating a disease state characterized by the presence of cells that have a deficient innate anti-viral response, comprising administering to a patient in need thereof an effective amount of a combination of Myxoma virus and rapamycin.

The present invention further provides use of an effective amount of a combination of Myxoma virus and rapamycin for inhibiting a cell that has a deficient innate anti-viral response and for the manufacture of a medicament for inhibiting a cell that has a deficient innate anti-viral response.

The present invention further provides use of an effective amount of a combination of Myxoma virus and rapamycin for treating a disease state in a patient, wherein the disease state is characterized by the presence of cells that have a deficient innate anti-viral response and for the manufacture of a medicament for treating such a disease state in a patient.

In another aspect, the present invention provides a pharmaceutical composition comprising Myxoma virus and rapamycin. The pharmaceutical composition may be useful for inhibiting a cell that has a deficient innate anti-viral response or for treating a disease state characterized by the presence of cells that have a deficient innate anti-viral response.

In another aspect, the present invention provides a kit comprising Myxoma virus, rapamycin and instructions for inhibiting a cell that has a deficient innate anti-viral response or for treating a disease state characterized by the presence of cells that have a deficient innate anti-viral response. The disease states include cancer and a chronic viral infection.

The present invention further provides a method of detection a cell that has a deficient innate anti-viral response, comprising exposing a population of cells to a combination of Myxoma virus and rapamycin; allowing the virus to infect a cell that has a deficient innate anti-viral response; and determining the infection of any cells of the population of cells by the Myxoma virus.

The present invention is further based on the unexpected discovery that rabbit Myxoma virus protein M135R is involved in eliciting an immune response in rabbits and that a Myxoma virus strain that does not express functional M135R can kill cells in vitro, but does not cause myxomatosis disease in animals. Such a viral strain can be used to treat cells having a deficient innate anti-viral response, including those that are non-responsive to interferon, and including treatments given in combination with the drug rapamycin, without the need for increased containment of the virus, leading to improved safety.

In one aspect, the present invention provides a method for inhibiting a cell that has a deficient innate anti-viral response comprising administering to the cell an effective amount of Myxoma virus that does not express functional M135R, optionally in combination with an effective amount of rapamycin.

In one aspect, the invention provides a method for treating a disease state characterized by the presence of cells that have a deficient innate anti-viral response, comprising administering to a patient in need thereof an effective amount of Myxoma virus that does not express functional M135R, optionally in combination with an effective amount of rapamycin.

The present invention further provides use of an effective amount of Myxoma virus that does not express functional M135R, optionally in combination with an effective amount of rapamycin, for inhibiting a cell that has a deficient innate anti-viral response and in the manufacture of a medicament for inhibiting a cell that has a deficient innate anti-viral response.

The present invention further provides use of an effective amount of Myxoma virus that does not express functional M135R, optionally in combination with an effective amount of rapamycin, for treating a disease state in a patient, wherein the disease state is characterized by the presence of cells that have a deficient innate anti-viral response and in the manufacture of a medicament for treating such a disease state in a patient.

In a further aspect, the present invention provides a Myxoma virus that does not express functional M135R.

In another aspect, the present invention provides a pharmaceutical composition comprising Myxoma virus that does not express functional M135R. The pharmaceutical composition may be useful for inhibiting a cell that has a deficient innate anti-viral response or for treating a disease state characterized by the presence of cells that have a deficient innate anti-viral response. The pharmaceutical composition may further comprise rapamycin.

In another aspect, the present invention provides a kit comprising Myxoma virus that does not express functional M135R and instructions for inhibiting a cell that has a deficient innate anti-viral response or for treating a disease state characterized by the presence of cells that have a deficient innate anti-viral response. The kit may further comprise rapamycin. The disease state includes cancer and a chronic viral infection.

The present invention further provides a method for detecting a cell that has a deficient innate anti-viral response, comprising exposing a population of cells to a Myxoma virus that does not express functional M135R, optionally in combination with rapamycin; allowing the virus to infect a cell that has a deficient innate anti-viral response; and determining the infection of any cells of the population of cells by the Myxoma virus.

Other aspects and features of the present invention will become apparent to those of ordinary skill in the art upon review of the following description of specific embodiments of the invention in conjunction with the accompanying figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

In the figures, which illustrate embodiments of the present invention, by way of example only.

DETAILED DESCRIPTION

Figure 1:
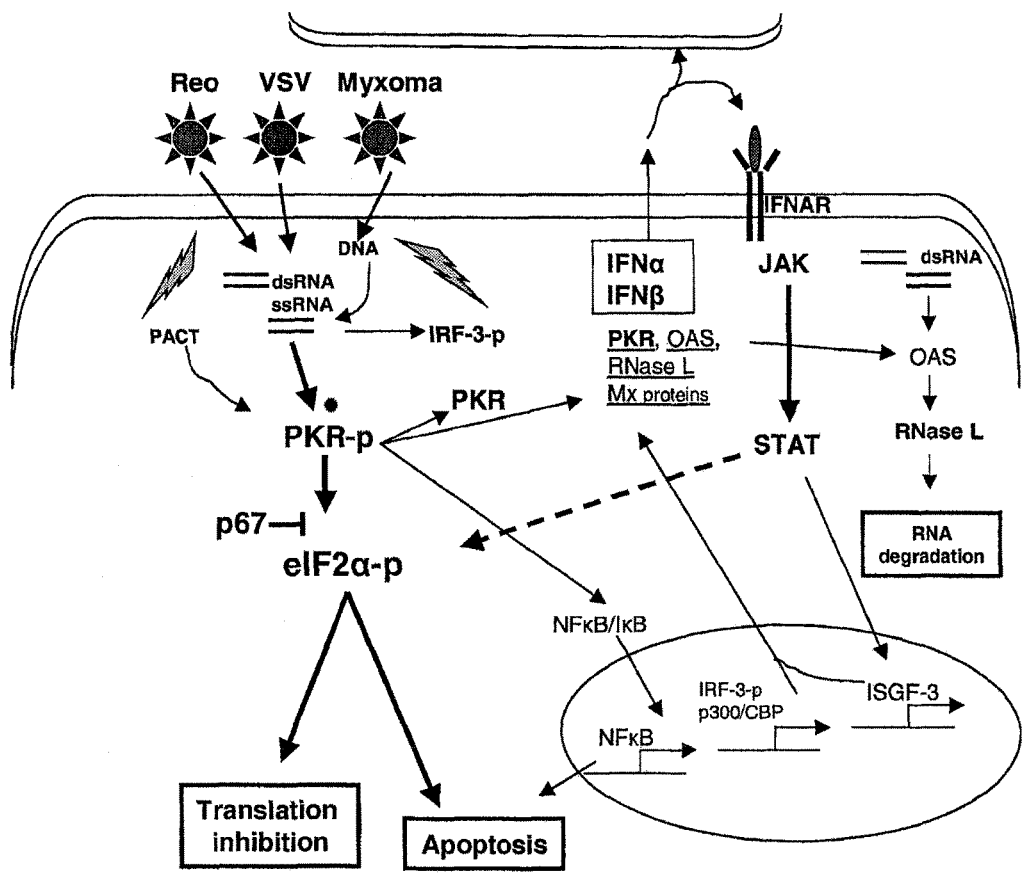
FIG. 1 is a schematic diagram of an interferon mediated anti-viral signalling scheme induced upon viral infection of a cell.

Previously, the inventors have discovered that wildtype Myxoma virus, a virus that normally infects rabbits, can selectively infect and kill cells, including human cells, that have a deficient innate anti-viral response, for example, cells that are non-responsive to interferon, as described in the application PCT/CA2004/000341, which is herein fully incorporated by reference. Myxoma virus does not replicate efficiently in normal human cells. Since many diseases or conditions are characterized by the presence of cells that have a deficient innate anti-viral response, including cells that are not responsive to interferon, for example, cancer, Myxoma virus can be used to treat such diseases and conditions, including cancer, with low toxicity for normal healthy cells. Myxoma virus can also be used to treat chronically infected cells as such cells have a deficient innate anti-viral response. For example, many viruses encode gene products that function to inhibit the antiviral, interferon response of cells; Myxoma virus can selectively infect such cells.

Myxoma virus ("MV") is the causative agent of myxomatosis in rabbits. MV belongs to the *Leporipoxvirus* genus of the Poxyiridae family, the largest of the DNA viruses. MV induces a benign disease in its natural host, the *Sylvilagus* rabbit in the Americas. However, it is a virulent and host-specific poxvirus that causes a fatal disease in European rabbits, characterized by lesions found systemically and especially around the mucosal areas. (Cameron C, Hota-Mitchell S, Chen L, Barrett J, Cao J X, Macaulay C, Willer D, Evans D, McFadden G. *Virology* 1999, 264(2): 298-318; Kerr P & McFadden G. *Viral Immunology* 2002, 15(2): 229-246).

MV is a large virus with a double-stranded DNA genome of 163 kb which replicates in the cytoplasm of infected cells (B. N. Fields, D. M. Knipe, P. M. Howley, Eds., *Virology* Lippincott Raven Press, New York, 2nd ed., 1996). MV is known to encode a variety of cell-associated and secreted proteins that have been implicated in down-regulation of the host's immune and inflammatory responses and inhibition of apoptosis of virus-infected cells. MV can be taken up by all human somatic cells. However, other than in normal somatic rabbit cells, if the cells have a normal innate anti-viral response, the virus will not be able to productively infect the cell, meaning the virus will not be able to replicate and cause cell death.

Interferons ("IFNs") are a family of cytokines that are secreted in response to a variety of stimuli. Interferons bind to cell surface receptors, activating a signaling cascade that leads to numerous cellular responses, including an anti-viral response and induction of growth inhibition and/or apoptotic signals. Interferons are classified as either type I or type II. Type I IFNs include IFN-α, -β, -τ, and ω, which are all monomeric; the only type II IFN is IFN-γ, a dimer. Twelve different subtypes of IFN-α are produced by 14 genes, but all other IFNs are monogenic (Arduini et al., 1999). IFNs exert direct anti-tumour activity via the modulation of oncogene expression. Overexpression of growth-stimulating oncogenes or loss of tumour suppressor oncogenes can lead to malignant transformation. Some oncogenes implicated in the genesis of cancer are p53, Rb, PC, NF1, WT1, DCC.

Myxoma virus, as well as other oncolytic viruses such as Reovirus and VSV, needs to bypass the anti-viral defenses that exist in normal healthy cells in order to be able to replicate within cells. MV and other oncolytic viruses induce interferon production, and are generally sensitive to the anti-viral effect of the IFN pathway. Relevant proteins induced by the IFN anti-viral response, and which principally affect virus multiplication include PKR, OAS synthetase and Rnase L nuclease. PKR activates eIF2α, leading to inhibition of translation and induction of apoptosis. A schematic representation of the IFN response pathway is depicted in FIG. 1. In normal cells, MV is directly affected by PKR and eIF2α.

Anti-viral response pathways are often disrupted in cancerous cells. For example, reduced or defective response to IFN is a genetic defect that often arises during the process of transformation and tumour evolution. Over 80% of tumour cell lines do not respond to, or exhibit impaired responses to, interferon. (Stojdl et al., *Cancer Cell* (2003) 4: 263-275 and references cited therein; Wong et al. *J Biol. Chem.* (1997) 272(45):28779-85; Sun et al. *Blood*. (1998) 91(2):570-6; Matin et al. *Cancer Res*. (2001) 61(5):2261-6; Balachandran et al *Cancer Cell* (2004) 5(1):51-65). As previously disclosed in PCT/CA2004/000341, MV can infect and kill cancer cells, including human tumour cells, and without being limited by any particular theory, it is believed that MV can infect these cells because they have a deficient innate anti-viral response.

Evidence suggests that inhibiting the early innate immune response and slowing the development of Th1 responses are important for the efficacy of oncolytic therapy. Although Myxoma virus is a virulent virus, it is host-specific and has a very narrow host range; it does not infect humans or mice. Without being limited by any specific theory, it is believed that since Myxoma virus is a non-human virus, it should encounter no pre-existing immune recognition in humans. Therefore, its potential as an oncolytic virus will be less compromised and Myxoma virus should provide more potent infection of permissive tumour cells than native human viruses, and thereby can provide an effective oncolytic treatment for cancer.

The Myxoma virus host range gene M-T5 appears to play a critical role during Myxoma virus infection of many human tumour cell lines (Sypula et al, (2004) *Gene Ther. Mol. Biol.* 8:103). The MT-5 gene encodes an ankyrin repeat protein that is required for Myxoma replication in rabbit lymphocytes, and Myxoma virus with the MT-5 gene deleted cannot cause myxomatosis in susceptible rabbits (Mossman et al, (1996) *J. Virol.* 70: 4394). Available evidence suggests that differences in the intracellular signalling within an infected human tumour cell are critical for distinguishing human tumour cells that are permissive to Myxoma virus infection and productive replication (Johnston et al, (2003) *J. Virol.* 77: 5877).

Furthermore, Myxoma virus possesses a protein, M135R, which displays homology to the amino terminus portion of interferon α/β receptor ("IFNα/β-R"). It has been suggested that M135R mimics the host IFNα/β-R in order to prevent IFNα/β from triggering a host anti-viral response (Barrett et al., *Seminars in Immunology* (2001) 13:73-84). The prediction is based on sequence homology to the viral IFNα/β-R from vaccinia virus, B18R, and it has been demonstrated that Vaccinia virus ("VV") employs such an immune evasion strategy. However, M135R is only half the size of VV B18R and all other IFNα/β-R homologs from sequenced poxviruses, and in all cases aligns only to the amino terminus half of the homolog.

The inventors have discovered that even though immunofluorescence results suggest that M135R localizes to the cell surface, attempts to demonstrate the ability of M135R to interact with IFNα/β have been negative. Despite these results, the inventors have discovered that deletion of M135R severely attenuates the ability of Myxoma virus to cause disease in host animals although Myxoma virus having such a deletion is equally effective at infecting and killing cells in vitro compared to wildtype MV. Thus, in one aspect, the present invention relates to the discovery that Myxoma virus that does not express functional M135R is useful for treatment of cells having a deficient innate anti-viral response, including for oncolytic studies, since this virus provides a safer alternative for oncolytic viral therapy as no unusual containment strategies should be needed for patients undergoing treatment.

In another aspect, the present invention relates to the discovery that the anti-cancer agent rapamycin acts to enhance the levels of infectivity of Myxoma virus in human tumour cells which are permissive for Myxoma virus infection, and that rapamycin allows replication of certain strains of Myxoma virus in human tumour cells which, without rapamycin, are restrictive for the replication of those strains of Myxoma virus. A cell that is permissive for Myxoma virus infection is a cell that the virus can enter and in which the virus can productively reproduce. Permissive cells may have defects or mutations in one or more of the pathways that involve the proteins PTEN, PDK, AKT, GSK, Raf, mTOR or P70S6K. A restrictive cell is a cell which is permissive to Myxoma virus only under certain conditions, but does not allow productive infection under other conditions. For example, a restrictive cell may be permissive to wildtype strains of the virus, but does not allow certain mutant Myxoma strains, for example a strain having the MT-5 gene knocked out, to productively reproduce. In another example, a cell restrictive for Myxoma virus may not permit productive infection of Myxoma virus alone, but when treated with rapamycin, the same Myxoma virus is able to productively infect the cell. Abortive cell lines are non-permissive for Myxoma virus infection, meaning that the virus may be able to enter the cell, but does not productively infect the cell.

Thus, rapamycin, when used in combination with Myxoma virus, enhances the infectivity of Myxoma virus for cells having a deficient innate anti-viral response. The present invention relates to the use of rapamycin in combination with Myxoma virus to treat cells having a deficient innate anti-viral response.

Rapamycin is a macrocyclic lactone that has been shown to be the active antifungal compound purified from the soil bacterium *Streptomyces hygroscopicus*. Rapamycin as used herein refers to rapamycin (also referred to as sirolimus) and analogs or derivatives thereof capable of complexing with FKBP12 and inhibiting mTOR, including the analogs CCI-779 (also referred to as cell cycle inhibitor-779 or rapamycin-42,2,2-bis(hydroxymethyl)-propionic acid) and RAD001 (also referred to as everolimus or 40-O-(2-hydroxyethyl)-rapamycin). Rapamycin, CCI-779 and RAD001 are commercially available, and rapamycin is available under the name Rapamune™, from Wyeth-Ayerst. The term rapamycin further includes pharmaceutically acceptable salts and esters of rapamycin, its hydrates, solvates, polymorphs, analogs or derivatives, as well as pro-drugs or precursors which are metabolized or converted to rapamycin or its analogs or derivatives during use, for example when administered to a patient.

Rapamycin as an inhibitor of cellular signaling is highly specific: it enters the cell and binds to a cellular protein known as FKBP12. The rapamycin/FKBP12 complex then binds to the specific cellular target mTOR (mammalian Target of Rapamycin). Many cancers have been shown to develop from an over activity of signaling molecules such as P13K, or a loss of the tumor suppressor gene PTEN. Both of these molecules lie upstream of mTOR. mTOR has been shown to be a central regulator of cell proliferation, growth, differentiation, migration and survival, and is therefore an ideal target in stemming the uncontrolled growth of cancer cells. Cancer cell lines that are sensitive to rapamycin are generally those that have resulted from an activation of the pathway through mTOR.

Rapamycins are used primarily in transplant patients as an alternative or complementary treatment to cyclosporine treatment. In transplant patients, rapamycin treatment generally has fewer side effects that cyclosporine A or FK506. In addition, retrospective studies have indicated that patients on rapamycin treatment generally develop fewer cancers and have a lower incidence of CMV (cytomegalovirus; a herpes virus) infection. It is therefore surprising that rapamycin treatment enhances Myxoma virus infection of cancer cells, particularly in light of research postulating that CMV replication should be reduced by rapamycin (reviewed by Ponticelli: "The pleiotropic effects of mTOR inhibitors" in *J Nephrology* 2004; 17: 762). Without being limited to a particular theory, it is possible that Myxoma virus takes advantage of aberrant signaling through the mTOR pathway that may be associated with the neoplastic phenotype of these cells. Manipulation of this pathway by mTOR inhibitors could then be a selective advantage to the virus.

Thus, there is provided a method for inhibiting a cell that has a deficient innate anti-viral response comprising administering to the cell an effective amount of Myxoma virus. In a further embodiment, the virus is administered in combination with an effective amount of rapamycin.

The Myxoma virus may be any virus that belongs to the *Leporipoxvirus* species of pox viruses that is replication-competent. The Myxoma virus may be a wild-type strain of Myxoma virus or it may be a genetically modified strain of Myxoma virus, including an MT-5 knockout strain of Myxoma. The Myxoma virus may be a strain that has an attenuated affect in rabbits, thereby causing lower risk of disease, including a strain that does not express functional M135 protein, as described below.

In a particular embodiment, the Myxoma virus is a Myxoma virus that does not express functional M135R.

A Myxoma virus that does not express functional M135R includes a Myxoma virus that has part, or all, of the open reading frame that encodes M135R deleted, replaced or interrupted such that no gene product, no stable gene product, or no functional gene product is expressed. Such a virus also includes a Myxoma virus that has part, or all, of the M135R gene regulatory region deleted, replaced or interrupted such that no protein can be expressed from the gene encoding M135R. Functional M135R protein is M135R that is transcribed, translated, folded, post-translationally modified and localized within the cell, and which allows Myxoma virus to cause myxomatosis in an infected host. If the M135R protein is not, or not properly or not sufficiently, transcribed, translated, folded, post-translationally modified or localized within the cell such that an infected host does not develop myxomatosis, then no functional M135R protein is expressed in the cell.

In a further embodiment, the cell is non-responsive to interferon.

In specific embodiments, the cell is a mammalian cancer cell. In one embodiment the cell is a human cancer cell including a human solid tumour cell.

In another embodiment, the cell is chronically infected with a virus.

A "combination" of rapamycin and Myxoma virus for administration may be formulated together in the same dosage form or may be formulated in separate dosage forms, and the separate dosage forms may be the same form or different forms, for administration by the same mode or by different modes of administration. Furthermore, administration of a combination of rapamycin and Myxoma virus, when not together in the same dosage form, means that the rapamycin and Myxoma virus are administered concurrently to the mammal being treated, and may be administered at the same time or sequentially in any order or at different points in time. Thus, rapamycin and Myxoma virus may be administered separately but sufficiently closely in time so as to provide the desired therapeutic effect.

The term "effective amount" as used herein means an amount effective, at dosages and for periods of time necessary to achieve the desired result.

The term "a cell that has a deficient innate anti-viral response" as used herein refers to a cell that, when exposed to a virus or when invaded by a virus, does not induce anti-viral defence mechanisms, which include inhibition of viral replication, production of interferon, induction of the interferon response pathway, and apoptosis, which may or may not be mediated by interferon, and is thereby infectable by MV, alone or in combination with rapamycin treatment. The term includes a cell that has a reduced or defective innate anti-viral response upon exposure to or infection by a virus as compared to a normal cell, for example, a non-infected, or non-cancer cell. This includes a cell that is non-responsive to interferon and a cell that has a reduced or defective apoptotic response or induction of the apoptotic pathway. The deficiency may be caused by various causes, including infection, genetic defect, or environmental stress. It will however be understood that when the deficiency is caused by a pre-existing infection, superinfection by MV may be excluded and a skilled person can readily identify such instances. A skilled person can readily determine without undue experimentation whether any given cell type has a deficient innate anti-viral response and therefore infectable by Myxoma virus, either alone or in combination with rapamycin treatment. For example, VSV is commonly used to measure an anti-viral response of a cell.

To assess whether a given cell type, for example a given cancer cell type, has a deficient innate anti-viral response, a skilled person can take an explant, grow some of the cells in vitro and determine infectability by VSV or alternatively, by Myxoma virus, including Myxoma virus in combination with rapamycin.

The term "a cell that is non-responsive to interferon" as used throughout the specification means a cell that does not respond to the activity of interferon, for example anti-viral or anti-tumour activity of interferon or that has an abnormal interferon response, for example, a reduced or ineffective response to interferon, or abnormal interferon signalling as measured by, for example, phosphorylation or activation of signalling molecules such as transcription factors, for example STAT1. For example, without limitation, the cell may not undergo inhibition of proliferation or it may not be killed when exposed to interferon levels sufficient to induce such a response in a cell that is responsive to interferon. The cell that is non-responsive to interferon may have a defect in the intracellular signalling pathway or pathways that are normally activated in the responsive cells. Typically, susceptibility to infection by VSV is indicative of non-responsiveness to interferon, and a skilled person can readily determine whether a particular cell is non-responsive to interferon by its ability, or lack thereof, to inhibit VSV infection in the presence of interferon or using other markers of interferon activity known in the art, for example, the level of expression of IFN stimulated genes such as PKR, STAT, OAS, MX.

The term "replication-competent" as used throughout the specification refers to a virus that is capable of infecting and replicating within a particular host cell. This includes a virus which alone is restricted for replication in a particular host cell, but when the host cell is treated with rapamycin, the virus can then productively infect that cell.

The term "a cell" as used herein includes a single cell as well as a plurality or population of cells. Administering an agent to a cell includes both in vitro and in vivo administrations.

The term "animal" as used herein includes all members of the animal kingdom, including particularly mammals, especially humans.

The term "inhibiting" a cell that has a deficient innate anti-viral response includes cell death by lysis or apoptosis or other mechanisms of cell death, in addition to rendering the cell incapable of growing or dividing or reducing or retarding cell growth or division.

The Myxoma virus genome may be readily modified to express one or more therapeutic transgenes using standard molecular biology techniques known to a skilled person, and described for example in Sambrook et al. ((2001) Molecular Cloning: a Laboratory Manual, $3^{rd}$ ed., Cold Spring Harbour Laboratory Press). A skilled person will be able to readily determine which portions of the Myxoma viral genome can be deleted such that the virus is still capable of productive infection. For example, non-essential regions of the viral genome that can be deleted can be deduced from comparing the published viral genome sequence with the genomes of other well-characterized viruses (see for example C. Cameron, S. Hota-Mitchell, L. Chen, J. Barrett, J.-X. Cao, C. Macaulay, D. Willer, D. Evans, and G. McFadden, *Virology* (1999) 264: 298-318)).

The term "therapeutic gene" or "therapeutic transgenes" as used herein is intended to describe broadly any gene the expression of which effects a desired result, for example, anti-cancer effect. For example, the virus may be modified to carry a gene that will enhance the anti-cancer effect of the viral treatment. Such a gene may be a gene that is involved in triggering apoptosis, or is involved in targeting the infected cell for immune destruction, such as a gene that repairs a lack of response to interferon, or which results in the expression of a cell surface marker that stimulates an antibody response, such as a bacterial cell surface antigen. The virus may also be modified to express genes involved in shutting off the neoplastic or cancer cell's proliferation and growth, thereby preventing the cells from dividing. As well, the virus may be modified to include therapeutic genes, such as genes involved in the synthesis of chemotherapeutic agents, or it may be modified to have increased replication levels in cells of the particular species from which the cells to be inhibited or killed are derived, for example, human cells. Specific examples of genes that may be inserted into the Myxoma virus to increase its anti-cancer effect include the human gene for the TRAIL protein or the adenoviral gene that encodes the E4 orf4 polypeptide, both of which proteins are involved in killing human tumour cells.

It will be understood that therapeutic effect of the Myxoma virus, including when used in combination with rapamycin, may be achieved by cell lysis by the virus or by delivery of therapeutic products by the virus. The inclusion of rapamycin in combination with the Myxoma virus should allow for enhancement of the effect of Myxoma virus alone. That is, the Myxoma virus, when administered in combination with rapamycin should be able to productively infect a greater number of target cells than Myxoma virus alone, or should be able to productively infect target cells having a deficient innate anti-viral response which are restrictive for productive infection by Myxoma virus in the absence of rapamycin.

The virus may be prepared using standard techniques known in the art. For example, the virus may be prepared by infecting cultured rabbit cells with the Myxoma virus strain that is to be used, allowing the infection to progress such that the virus replicates in the cultured cells and can be released by standard methods known in the art for disrupting the cell surface and thereby releasing the virus particles for harvesting. Once harvested, the virus titre may be determined by infecting a confluent lawn of rabbit cells and performing a plaque assay (see Mossman et al. (1996) *Virology* 215:17-30).

There is also provided a method for treating a disease state characterized by the presence of cells that have a deficient innate anti-viral response in a patient in need of such treatment comprising administering to the patient an effective amount of Myxoma virus, optionally in combination with rapamycin. The patient may be any animal, including a mammal, including a human.

"A disease state characterized by the presence of cells that have a deficient innate anti-viral response" as used herein refers to any disease, disorder or condition which is associated with, related to, or a characteristic of which is, the presence of cells that have a deficient innate anti-viral response and which disease, disorder, condition or symptoms thereof may be treated by killing these cells. For example, the disease state may be cancer. The disease state may also include chronic infection with a virus.

"Treating" a disease state refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of development of disease, prevention of spread of disease, delay or slowing of disease progression, delay or slowing of disease onset, amelioration or palliation of the disease state, and remission (whether partial or total). "Treating" can also mean prolonging survival of a patient beyond that expected in the absence of treatment. "Treating" can also mean inhibiting the progression of disease, slowing the progression of disease temporarily, although more preferably, it involves halting the progression of the disease permanently.

In one embodiment, the disease state is cancer. The cancer may be any type of cancer wherein at least some of the cells, although not necessarily all of the cells have a deficient innate anti-viral response. In one embodiment, the cancer may be a cancer wherein at least some of the cells are non-responsive to interferon. As used herein, the terms "tumour", "tumour cells", "cancer" and "cancer cells", (used interchangeably) refer to cells that exhibit abnormal growth, characterized by a significant loss of control of cell proliferation or cells that have been immortalized. The term "cancer" or "tumour" includes metastatic as well as non-metastatic cancer or tumours. As used herein, "neoplastic" or "neoplasm" broadly refers to a cell or cells that proliferate without normal growth inhibition mechanisms, and therefore includes benign tumours, in addition to cancer as well as dysplastic or hyperplastic cells.

A cancer may be diagnosed using criteria generally accepted in the art, including the presence of a malignant tumor.

Types of cancer that may be treated according to the present invention include, but are not limited to, hematopoietic cell cancers including leukemias and lymphomas, colon cancer, lung cancer, kidney cancer, pancreas cancer, endometrial cancer, thyroid cancer, oral cancer, ovarian cancer, laryngeal cancer, hepatocellular cancer, bile duct cancer, squamous cell carcinoma, prostate cancer, breast cancer, cervical cancer, colorectal cancer, melanomas and any other tumours. Solid tumours such as sarcomas and carcinomas include but are not limited to fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In another embodiment, the disease state is a chronic viral infection.

The chronically infecting virus may be any virus that infects and replicates in cells of an animal in a persistent manner over a prolonged period so as to cause a pathological condition. The chronically infecting virus may be a virus that is associated or correlated with the development of cancer.

A chronic infection with a virus may be diagnosed using standard methods known in the art. For example, a chronic viral infection may be detected by the presence of anti-viral antibodies in the patient or a positive test for the presence of viral RNA or DNA in cells of the patient.

When administered to a patient, an effective amount of the Myxoma virus, and optionally the combination of Myxoma virus with rapamycin, is the amount required, at the dosages and for sufficient time period, for the virus to alleviate, improve, mitigate, ameliorate, stabilize, prevent the spread of, slow or delay the progression of or cure the disease. For example, it may be an amount sufficient to achieve the effect of reducing the number of or destroying cancerous cells or neoplastic cells, or reducing the number of or destroying cells chronically infected with a virus, or inhibiting the growth and/or proliferation of such cells.

The effective amount to be administered to a patient can vary depending on many factors such as the pharmacodynamic properties of the Myxoma virus and the optionally rapamycin, the modes of administration, the age, health and weight of the patient, the nature and extent of the disease state, the frequency of the treatment and the type of concurrent treatment, if any, and the virulence and titre of the virus.

One of skill in the art can determine the appropriate amount of Myxoma virus for administration based on the above factors. The virus may be administered initially in a suitable amount that may be adjusted as required, depending on the clinical response of the patient. The effective amount of virus can be determined empirically and depends on the maximal amount of the virus that can be administered safely, and the minimal amount of the virus that produces the desired result.

Myxoma virus may be administered to the patient using standard methods of administration. In one embodiment, the virus is administered systemically. In another embodiment, the virus is administered by injection at the disease site. In a particular embodiment, the disease state is a solid tumour and the virus is administered by injection at the tumour site. In various embodiments, the virus may be administered orally or parenterally, or by any standard method known in the art.

To produce the same clinical effect when administering the virus systemically as that achieved through injection of the virus at the disease site, administration of significantly higher amounts of virus may be required. However, the appropriate dose level should be the minimum amount that would achieve the desired result.

The concentration of virus to be administered will vary depending on the virulence of the particular strain of Myxoma that is to be administered and on the nature of the cells that are being targeted. In one embodiment, a dose of less than about $10^9$ plaque forming units ("pfu") is administered to a human patient. In various embodiments, between about $10^2$ to about $10^9$ pfu, between about $10^2$ to about $10^7$ pfu, between about $10^3$ to about $10^6$ pfu, or between about $10^4$ to about $10^5$ pfu may be administered in a single dose.

One of skill in the art can also determine, using the above factors, the appropriate amount of rapamycin to administer to a patient. The effective amount of rapamycin can be determined empirically and will depend on the amount and strain of virus being administered, the maximum amount of rapamycin that can be safely administered and the minimal amount of rapamycin that can be administered in order to achieve an enhancement of the infectivity of Myxoma virus.

Rapamycin may be administered to the patient using standard methods of administration. In one embodiment, the rapamycin is administered systemically. In another embodiment, the rapamycin is administered by injection at the disease site. In a particular embodiment, the disease state is a solid tumour and the rapamycin is administered by injection at the tumour site. In various embodiments, the rapamycin may be administered orally or parenterally, or by any standard method known in the art.

The total amount of rapamycin may be administered in a single dose or in multiple doses spread out over 1 day or several days. The frequency and duration of administration of doses can be readily determined. The schedule of dosing will depend on the length of time that the Myxoma virus is to be administered. For example, rapamycin may be administered once to a patient, or may be administered 2 to 4 times per day.

In various embodiments, the dose of rapamycin may be from about 0.01 to about 250 mg per kg of body weight per day, from about 0.01 to 50 mg per kg of body weight per day, from about 0.05 to 10 mg per kg of body weight per day, or from about 0.1 to 7.5 mg per kg of body weight per day.

Effective amounts of a combination of Myxoma virus and rapamycin can be given repeatedly, depending upon the effect of the initial treatment regimen. Administrations are typically given periodically, while monitoring any response. It will be recognized by a skilled person that lower or higher dosages than those indicated above may be given, according to the administration schedules and routes selected.

The Myxoma virus, optionally in combination with rapamycin, may be administered as a sole therapy or may be administered in combination with other therapies, including chemotherapy, radiation therapy or other anti-viral therapies. For example, the Myxoma virus, optionally in combination with rapamycin, may be administered either prior to or following surgical removal of a primary tumour or prior to, concurrently with or following treatment such as administration of radiotherapy or conventional chemotherapeutic drugs. In one embodiment, the Myxoma virus, optionally in combination with rapamycin can be administered in combination with, or in a sequential fashion with, other oncolytic viruses, which may demonstrate specificity for varying tumour cell types.

To aid in administration, the Myxoma virus, optionally in combination together with rapamycin, may be formulated as an ingredient in a pharmaceutical composition. Therefore, in a further embodiment, there is provided a pharmaceutical composition comprising Myxoma virus, and optionally rapamycin, and a pharmaceutically acceptable diluent. The invention in one aspect therefore also includes such pharmaceutical compositions for use in inhibiting a cell that has a deficient innate anti-viral response or treating a disease state characterized by the presence of cells that have a deficient innate anti-viral response. The compositions may routinely contain pharmaceutically acceptable concentrations of salt, buffering agents, preservatives and various compatible carriers. For all forms of delivery, the recombinant Myxoma virus may be formulated in a physiological salt solution.

The pharmaceutical compositions may additionally contain additional therapeutic agents, such as additional anticancer agents. In one embodiment, the compositions include a chemotherapeutic agent. The chemotherapeutic agent, for example, may be substantially any agent which exhibits an oncolytic effect against cancer cells or neoplastic cells of the patient and that does not inhibit or diminish the tumour killing effect of the Myxoma virus. For example, the chemotherapeutic agent may be, without limitation, an anthracycline, an alkylating agent, an alkyl sulfonate, an aziridine, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. Preferably, the chemotherapeutic agent is one that is known to be effective against the particular cell type that is cancerous or neoplastic.

The proportion and identity of the pharmaceutically acceptable diluent is determined by chosen route of administration, compatibility with a live virus, and where applicable compatibility with the chemical stability of rapamycin, and standard pharmaceutical practice. Generally, the pharmaceutical composition will be formulated with components that will not significantly impair the biological properties of the live Myxoma virus, or cause degradation of or reduce the stability or efficacy of the rapamycin where included.

The pharmaceutical composition can be prepared by known methods for the preparation of pharmaceutically acceptable compositions suitable for administration to patients, such that an effective quantity of the active substance or substances is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the Myxoma virus, optionally with rapamycin, in association with one or more pharmaceutically acceptable vehicles or diluents, and contained in buffer solutions with a suitable pH and iso-osmotic with physiological fluids.

The pharmaceutical composition may be administered to a patient in a variety of forms depending on the selected route of administration, as will be understood by those skilled in the art. The composition of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

The pharmaceutical composition may be administered orally, for example, with an inert diluent or with an assimilable carrier, or it may be enclosed in hard or soft shell gelatin capsules, or it may be compressed into tablets. For oral therapeutic administration, the Myxoma virus may be incorporated, optionally together with rapamycin, with an excipient and be used in the form of ingestible tablets, buccal tablets, troches, capsules, elixirs, suspensions, syrups, wafers and the like.

Solutions of Myxoma virus, optionally together with rapamycin, may be prepared in a physiologically suitable buffer. Under ordinary conditions of storage and use, these preparations contain a preservative to prevent the growth of microorganisms, but that will not inactivate the live virus. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999.

In different embodiments, the composition is administered by injection (subcuteanously, intravenously, intramuscularly, etc.) directly at the disease site, such as a tumour site, or by oral administration, alternatively by transdermal administration.

The forms of the pharmaceutical composition suitable for injectable use include sterile aqueous solutions or dispersion and sterile powders for the extemporaneous preparation of sterile injectable solutions or dispersions, wherein the term sterile does not extend to the live Myxoma virus itself that is to be administered. In all cases the form must be sterile and must be fluid to the extent that easy syringability exists.

The dose of the pharmaceutical composition that is to be used depends on the particular condition being treated, the severity of the condition, the individual patient parameters including age, physical condition, size and weight, the duration of the treatment, the nature of concurrent therapy (if any), the specific route of administration and other similar factors that are within the knowledge and expertise of the health practitioner. These factors are known to those of skill in the art and can be addressed with minimal routine experimentation.

The Myxoma virus, optionally in combination with rapamycin, or pharmaceutical compositions comprising the Myxoma virus and rapamycin, either together in the same formulation or different formulations, may also be packaged as a kit, containing instructions for use of Myxoma virus and rapamycin, including the use of Myxoma virus, or use of Myxoma virus in combination with rapamycin, to inhibit a cell that has a deficient innate anti-viral response, or use of Myxoma virus, or use of Myxoma virus in combination with rapamycin, to treat a disease state characterized by the presence of cells that have a deficient innate anti-viral response, in a patient in need thereof. The disease state may be cancer, or it may be a chronic viral infection.

The present invention also contemplates the use of Myxoma virus, optionally in combination with rapamycin, for inhibiting a cell that has a deficient innate anti-viral response. In one embodiment, the cell is non-responsive to interferon. There is further provided use of Myxoma virus, optionally in combination with rapamycin, for treating a disease state characterized by the presence of cells that have a deficient innate anti-viral response, in a patient in need thereof. In one embodiment the disease state is cancer.

There is also provided use of Myxoma virus, optionally in combination with rapamycin, in the manufacture of a medicament, for inhibiting a cell that has a deficient innate anti-viral response, or for treating a disease state characterized by the presence of cells that have a deficient innate anti-viral response in a patient in need thereof.

MV can selectively infect cells in or derived from animals other than the natural host of MV, from a population of cells, which have a deficient innate anti-viral response. This ability of MV provides for the use of MV in detecting cells from a population of cells, either in culture or in an animal, that have a deficient innate anti-viral response, including cells that are non-responsive to interferon. Such cells may otherwise not be easily detectable, for example certain cancer cells that have not yet advanced to palpable tumour, or have not yet induced noticeable symptoms in the animal.

Thus, in one embodiment, there is provided a method for detecting cells that have a deficient innate anti-viral response in a patient, comprising administering to the patient Myxoma virus modified to express a detectable marker, optionally in combination with rapamycin; allowing the virus to infect a cell that has a deficient innate anti-viral response in the patient; and detecting the cell expressing the detectable marker in the patient.

The infected cells may be detected using any conventional method for visualizing diagnostic images. The method of detection will depend on the particular detectable marker that is used. For example, cells infected with Myxoma virus genetically modified to express a fluorescent protein may be detected using fluorescence digital imaging microscopy. Other methods include computed tomography (CT), whole body scan such as position emission tomography (PET), magnetic resonance imaging (MRI), and sonography. Skilled artisans will be able to determine the appropriate method for detecting a particular detectable marker.

The detectable marker includes, but is not limited to, any marker for which genes for its expression or synthesis can be inserted into the Myxoma genome so as to result in expression or synthesis of the marker within cells that are infected by the modified virus. For example, in one embodiment, the detectable marker may be a fluorescent protein. The infected cells may be detected at a suitable time interval after administration of the modified virus to the patient, so as to allow for the virus to infect any cells that have a deficient innate anti-viral response, and to express the detectable marker in such cells at levels that would allow for detection. For example, detection may occur anywhere between 2 and 20 days following administration to the patient of the virus genetically modified to express a fluorescent protein.

The detecting method may be carried out repeatedly at intervals in a patient in order to monitor the presence of cells that have a deficient innate anti-viral response in that patient. For example, the method for detecting such cells using Myxoma virus may be carried out on a patient at 6 month, 1 year or 2 year intervals, as is necessary, depending on the nature of the cells that has a deficient innate anti-viral response and the nature of any disease state caused as a result of the presence of such cells in a patient. Repeating the method over a time period allows for monitoring of the progression or remission of disease state, or the spread of disease within the body of the patient.

Myxoma virus is capable of selectively infecting cells that have a deficient innate anti-viral response, and can be used as an indicator of such a deficiency in cells. Thus, cells removed from a patient may be assayed for deficiency in innate anti-viral response using the methods of the present invention. Such determination may indicate, when combined with other indicators, that the patient may be suffering from a particular disease state, for example, cancer.

In one embodiment therefore, there is provided a method for detecting in a sample a cell that has a deficient innate anti-viral response comprising culturing the cell, exposing cultured cells to Myxoma virus, optionally in combination with rapamycin; and determining infectivity of cells by Myxoma virus.

The cells may be removed from a subject, including a human subject, using known biopsy methods. The biopsy method will depend on the location and type of cell that is to be tested.

Cells are cultured according to known culturing techniques, and are exposed to MV, and optionally rapamycin, by adding live Myxoma virus, and optionally rapamycin, to the culture medium. Where Myxoma virus is added in combination with rapamycin, the virus and rapamycin may be added either simultaneously or sequentially. The multiplicity of infection ("MOI"), including in the presence of rapamycin, may be varied to determine an optimum MOI for a given cell type, density and culture technique, and a particular rapamycin concentration, using a positive control cell culture that is known to be infected upon exposure to MV.

The amount of rapamycin, and the timing of addition of rapamycin and Myxoma virus to the cultured cells may be varied depending on cell type, method of culturing and strain of virus. Such parameters can be readily tested and adjusted with minimal testing using routine methods.

Infectivity of the cultured cells by MV, including in the presence of rapamycin, may be determined by various methods known to a skilled person, including the ability of the MV to cause cell death. It may also involve the addition of reagents to the cell culture to complete an enzymatic or chemical reaction with a viral expression product. The viral expression product may be expressed from a reporter gene that has been inserted into the MV genome.

In one embodiment the MV may be modified to enhance the ease of detection of infection state. For example, the MV may be genetically modified to express a marker that can be readily detected by phase contrast microscopy, fluorescence microscopy or by radioimaging. The marker may be an expressed fluorescent protein or an expressed enzyme that may be involved in a colorimetric or radiolabelling reaction. In another embodiment the marker may be a gene product that interrupts or inhibits a particular function of the cells being tested.

The invention is further illustrated by the following non-limiting examples.

EXAMPLES

Example 1: Infection of Mouse and Human Cell Lines with Myxoma Virus

Virus Strains

Viral strains used include wildtype MV, MV modified to express either green fluorescence protein ("GFP") or β-galactosidase ("LacZ"), and killed ("dead") MV. Viruses were prepped and titred using standard techniques.

Cell Strains

Mouse experiments were performed using mouse embryo fibroblasts ("MEFs") derived from a wild-type mouse, and from the following mouse knockouts: IFNα/β receptor homozygous knockout; STAT1 homozygous knockout; PKR heterozygous; RNaseL heterozygous knockout; Mx1 heterozygous knockout; triple PKR/RNaseL/Mx1 homozygous knockout.

Human experiments were performed on BGMK control cells and human tumour cell lines HT29, HOP92, OVCAR4, OVCAR5, SK-MEL3, SK-MEL28, M14, SKOV3, PC3, DU145, CAKI-1, 786-0, T47D, MDAMB 435, SF04, U87, A172, U373, Daoy and D384 as described in Stojdl et al., *Cancer Cell* (2003) 4: 263-275.

Methods

Generally, assays and experiments were performed as described in Lalani et al. *Virology* (1999) 256: 233-245; Johnston et al. *J Virology* (2003) 77(13): 7682-7688; and Sypula et al. *Gen Ther Mol Biol* (2004) δ: 103.

For the in vivo mouse studies, nude mice were implanted with intracranial human gliomas U87. 15 days after implantation, mice were intratumourally injected with live or dead MV GFP, at a titre of $5 \times 10^6$, or mock-infected. 72 hours post-infection, animals were sacrificed, the brains removed, embedded in OCT (Optimal Cutting Temperature compound), and frozen sections were cut. Myxoma-GFP was visualized in whole brain sections by fluorescence microscopy. Sections were then fixed and stained with H&E (hemotoxylin and eosin) to visualize the tumor.

For human tumour cell assays, the tumours were trypsonized and plated immediately after surgery and infected with virus the next day at an MOI of 0.1, 1.0 or 10. Data was gathered regarding cytotoxicity and viral expression using phase microscopy and fluorescent microscopy, respectively, at 24 and 48 hours post-infection. Assays using the yellow tetrazolium salt MTT were performed to quantify the % cell survival (as a percentage of cells surviving mock infection) at 48, 72 or 96 hours post-infection.

Human pediatric medulloblastoma cell lines, Daoy and D384, were infected with 10 M.O.I. of Myxoma-GFP. 72 hours after infection, cell viability was measured using MTT.

Results: Infections of Mouse Cell Lines

Previous research showed that some clones of mouse 3T3 cells transfected with chemokine receptors were infectable by Myxoma virus while other clones were not. To investigate whether Myxoma virus tropism in other mouse cells was dependent on any particular receptors, we exploited primary mouse embryo fibroblasts (MEFs) from wild-type (WT) mice and various gene knock-outs.

Since IFNs play a key role in mounting anti-viral responses, we hypothesized that the restrictive phenotype was related to the "antiviral state" mediated by IFN. Disruption of the chain of events of the IFN system, neutralizing circulating IFN with antibodies or generating IFN receptor negative mice, or mice with deleted genes in the intracellular pathway of signal transmission, would severely compromise the host's resistance to the Myxoma virus which typically does not infect normal mouse cells.

In order to test this hypothesis we needed to demonstrate if the non-infectivity of Myxoma virus in the nonpermissive cells was due to the antiviral action of IFNs. Various MEF cell types having knock-outs of one or more proteins involved in intracellular IFN signaling response were tested for the effect of MV infection on the IFN pathway.

Figure 2:
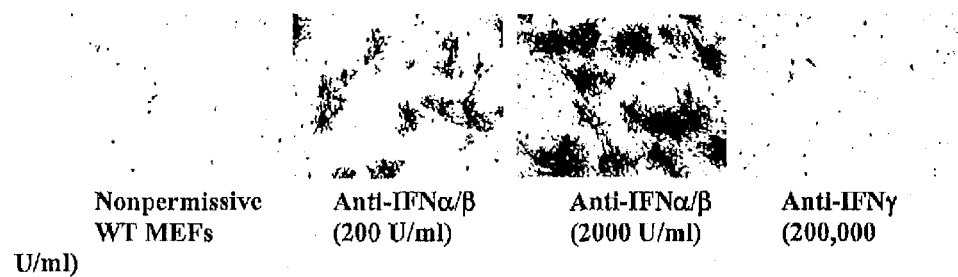
FIG. 2 is a phase contrast micrograph of nonpermissive WT murine embryonic fibroblasts ("MEFs") after exposure to Myxoma virus, demonstrating that the MEFs become permissive after inhibition of interferon α/β with neutralizing antibody.

Experiments performed on primary MEFs demonstrated that wildtype ("WT") MEFs are not infectable by Myxoma virus. The MEFs are fully infectable by Myxoma virus when the IFN pathway is blocked by neutralizing antibody to IFNα/β (FIG. 2). However, MEFs exposed to neutralizing antibodies to IFNγ remained nonpermissive. This outlined the importance of IFNα/β but not IFNγ in creating a permissive environment for Myxoma virus to infect MEFs in vitro. Different intracellular signaling pathways for IFNα/β and IFNγ have been identified in the literature. However, both IFNα/β and IFNγ likely play an important role in infected hosts, unlike cultured fibroblasts. We predict that human tumors deficient in either IFNα/β and/or IFNγ pathway will be susceptible to Myxoma virus infection in vivo.

Figure 4:
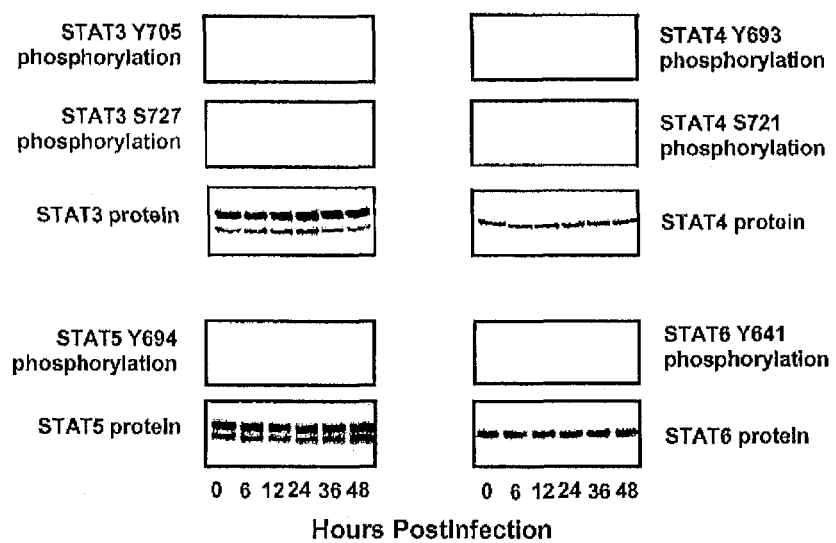
FIG. 4 is a Western blot showing phosphorylation states (inactivation) of STAT3, STAT4, STAT5 and STAT6 after Myxoma virus infection, demonstrating that nonpermissive infections of MEF cells does not activate any of these species.
Figure 3:
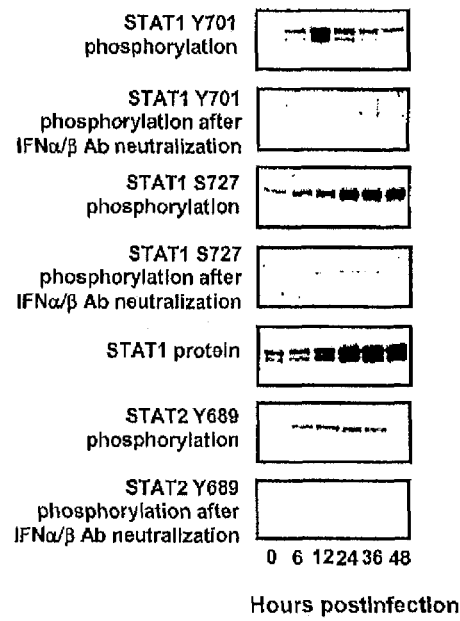
FIG. 3 is a Western blot showing phosphorylation states (activation) of STAT1 and STAT2 after Myxoma virus infection, demonstrating that nonpermissive infections of MEF cells is associated with activation of STAT 1 and STAT 2.

We examined the activity of STAT1 and STAT2 in nonpermissive WT MEFs that were infected with MV. The results shown in FIG. 3 indicated that STAT1 and STAT2 were activated. Further study showed that STAT3, STAT4 and STAT5 are not activated (FIG. 4).

Figure 5:
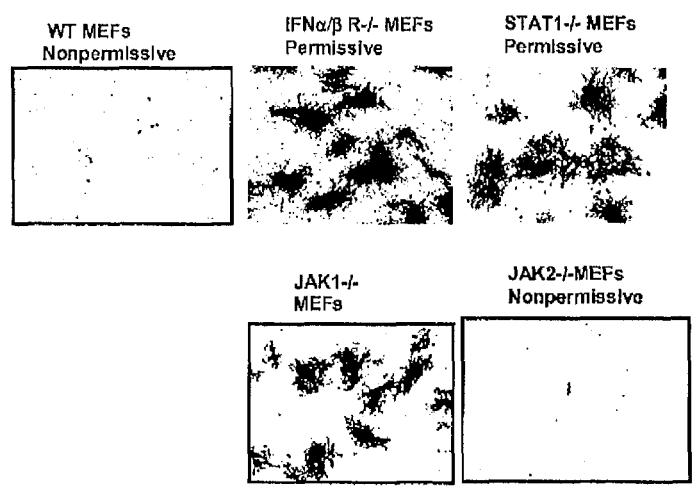
FIG. 5 is a phase contrast micrograph of IFNα/β R−/− MEFs and STAT1−/− MEFs, IFNα/β R−/− MEFs and STAT1−/− MEFs after infection with Myxoma virus, showing that inactivation of IFN/STAT/JAK signalling renders cells permissive for Myxoma infection.

In order to confirm the importance of the IFNα/β intracellular pathway in maintaining a nonpermissive state in MEFs, genetic deletion studies were performed to provide disruptions in the IFNα/β receptors and in the intracellular cascade. Genetic deletion of IFN receptors or JAK1 or STAT1 was performed. MV was used to infect WT MEFs, IFNα/β R–/– MEFs and STAT1–/– MEFs. IFNα/β R–/– MEFs and STAT1–/– MEFs were permissive to MV demonstrating the IFNα/β and STAT1 signalling cascades are critical for MV infection (FIG. 5).

Figure 6:
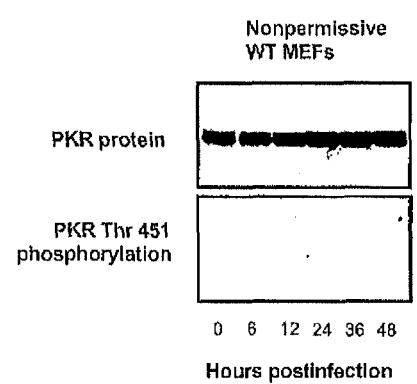
FIG. 6 is a Western blot showing phosphorylation states of PKR in nonpermissive wildtype MEFs after Myxoma virus infection, demonstrating that PKR is not activated by Myxoma virus infection.
Figure 7:
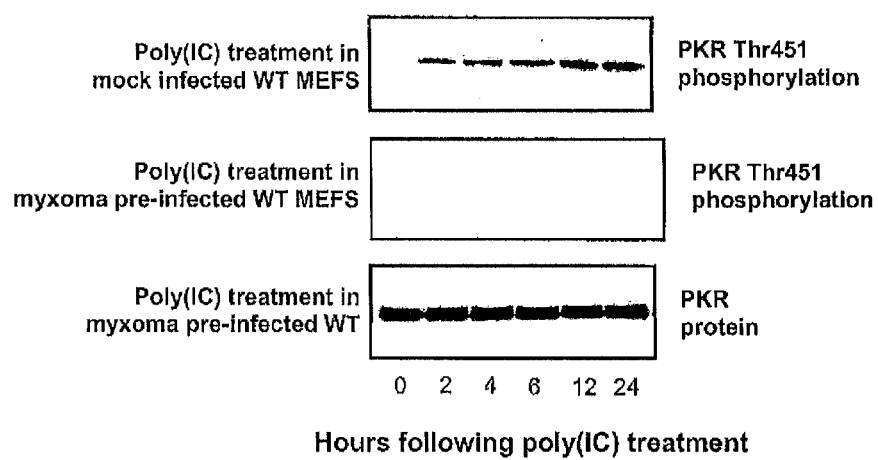
FIG. 7 is a Western blot showing phosphorylation states of PKR in wildtype MEFs either mock infected or pre-infected with Myxoma virus, showing that Myxoma virus blocks PKR activation in MEF cells.
Figure 8:
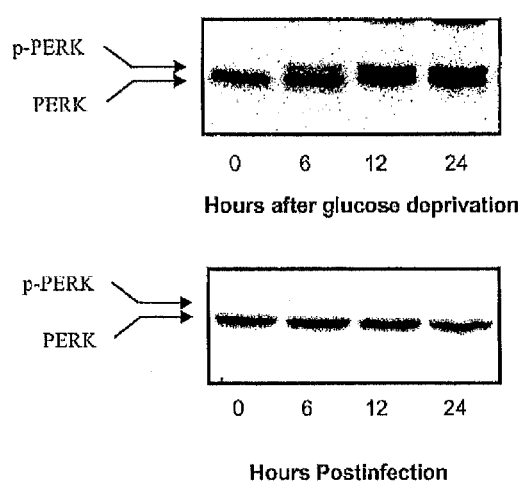
FIG. 8 is a Western blot showing phosphorylation states of PERK in wildtype MEFs after Myxoma virus infection, demonstrating that Myxoma virus blocks PERK activation in MEF cells.

Protein Kinase R (PKR) is an enzyme induced in a wide variety of cells by IFNα/β. This kinase, in the presence of dsRNA, undergoes autophosphorylation and then phosphorylates several cellular proteins including eukaryotic protein synthesis initiation factor (eIF-2α) whose phosphorylation can induces an inhibition of protein translation and apoptosis. PKR is also indicated in the activation of RNaseL. We examined the activation of PKR in nonpermissive MEFs following MV infection, PKR is not phosphorylated in nonpermissive MEFs in which the antiviral state is well established (FIG. 6). Furthermore MV infection inhibits PKR phosphorylation (FIG. 7). In addition, PERK (PKR-like, ER kinase) is not phosphorylated in the primary WT MEFs following Myxoma virus infection (FIG. 8).

Figure 9:
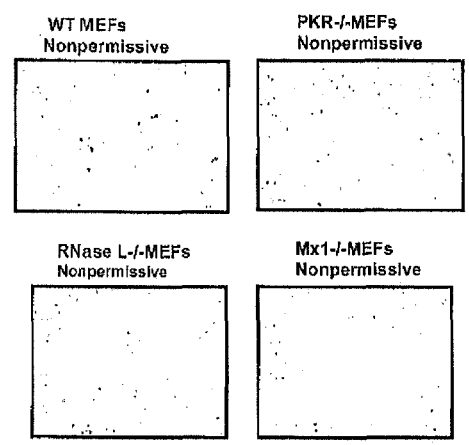
FIG. 9 is a phase contrast micrograph of PKR−/−, RNase L−/− and Mx1−/− triple knockout after exposure to Myxoma virus, showing that the antiviral state in MEF cells is mediated by a distinct pathway.
Figure 10:
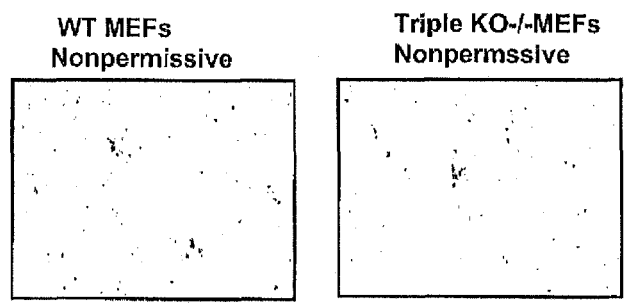
FIG. 10 is a phase contrast micrograph of PKR−/−, RNase L−/− and Mx1−/− triple knockout after exposure to Myxoma virus.
Figure 11:
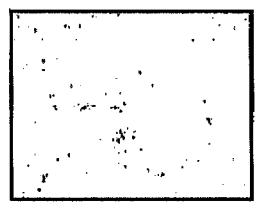
FIG. 11 is a phase contrast micrograph of PKR−/−, RNase L−/− and Mx1−/− triple knockout after treatment with neutralizing antibody to IFNα/β and after exposure to Myxoma virus.
Figure 11:
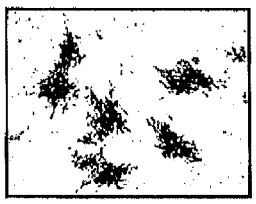

MV was use to infect MEFs with single gene knockouts of PKR, RNaseL or Mx1 (FIG. 9). It was discovered that PKR, RNaseL and Mx1 are nonessential for maintaining nonpermissiveness for Myxoma virus infection. To further confirm the nonessential role of PKR, RNaseL and Mx1 a Triple knockout of PKR–/–, RNase L–/– and Mx1–/– in MEFs was performed. A PKR–/–, RNase L–/– and Mx1–/– triple knockout does not support Myxoma virus infection (FIG. 10), however MEFs with a triple KO of PKR, RNaseL and Mx1 treated with a neutralizing antibody to Interferon α/β becomes permissive to Myxoma virus infection (compare FIGS. 10 and 11). These experiments demonstrate that PKR, RNaseL and Mx1 are not essential in mediating the nonpermissiveness of MEFs to MV.

Figure 12:
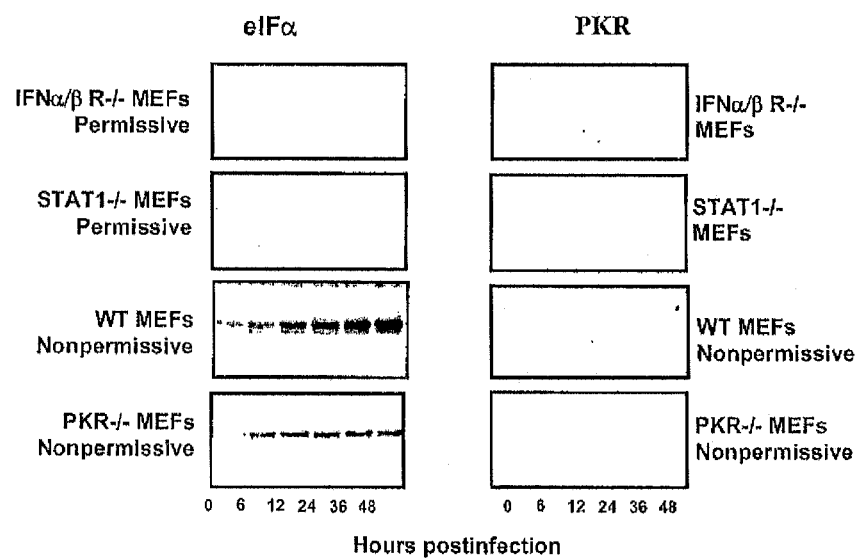
FIG. 12 is a Western blot showing phosphorylation levels of eIF2α and PKR in nonpermissive MEFs after treatment with neutralizing antibody to IFNα/β and after exposure to Myxoma virus, showing that eIF2α phosphorylation in nonresponsive cells is catalysed by a PKR-independent pathway.

Further studies were performed to examine the activation of eIF-2α and PKR in nonpermissive wildtype MEFs and permissive IFNα/β R–/– MEFs and STAT1–/–MEFs after MV infection. After MV infection, eIF-2α is phosphorylated in nonpermissive and permissive MEFs although PKR is not phosphorylated in either case (FIG. 12). This demonstrates that without the involvement of PKR and PERK, the antiviral state is mediated by another pathway that causes eIF2α phosphorylation.

Figure 13:
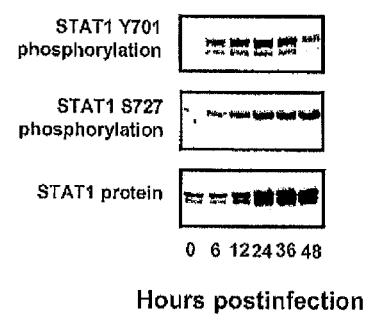
FIG. 13 is a Western blot showing STAT1 phosphorylation states in PKR−/−, RNase L−/− and Mx1−/− triple knockout after Myxoma virus infection, indicating normal IFN-induced signalling responses
Figure 14:
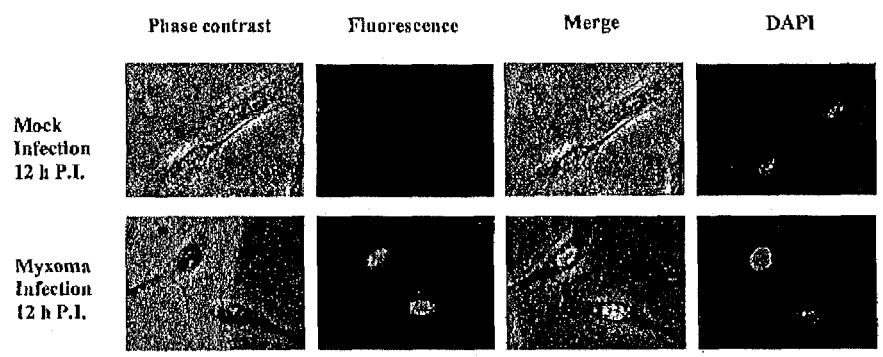
FIG. 14 is a phase contrast micrograph illustrating subcellular localization of tyrosine-phosphorylated STAT1 in nonpermissive PKR−/−+RNaseL−/−+Mx1−/− cells at 12 hours post-infection, indicating that the activated STAT localizes to the nucleus, as predicted for normal IFN/STAT signalling responses.

STAT1 is both serine- and tyrosine-phosphorylated following Myxoma infections in nonpermissive PKR, RNaseL and Mx1 Triple KO MEFs (FIG. 13). Subcellular localization of tyrosine-phosphorylated STAT1 in nonpermissive PKR–/–+RNaseL–/–+Mx1–/– MEFs following Myxoma virus infection is also shown (FIG. 14).

In summary, these results indicate that a parallel PKR/PERK-independent antiviral pathway involving IFN/STAT1 is critical for poxvirus tropism. Furthermore, eIF2α phosphorylation is the best marker for the antiviral action by INF.

Results: Human Tumour Studies

Figure 15:
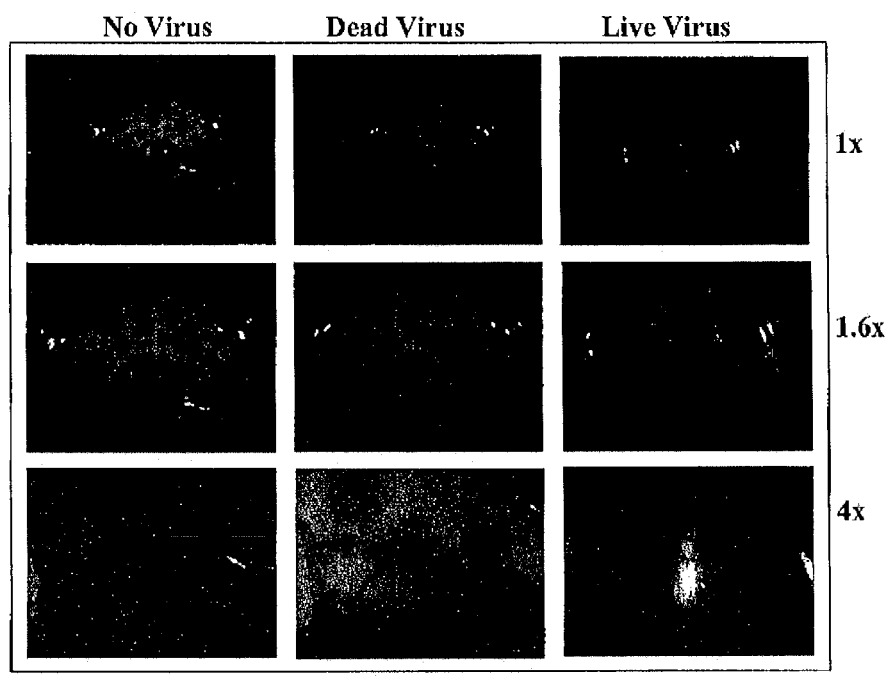
FIG. 15 is a fluorescent image of brains from nude mice having intracranial gliomas mock-infected or infected with dead or live Myxoma virus expressing GFP, showing targeting of Myxoma to the glioma cells.
Figure 16:
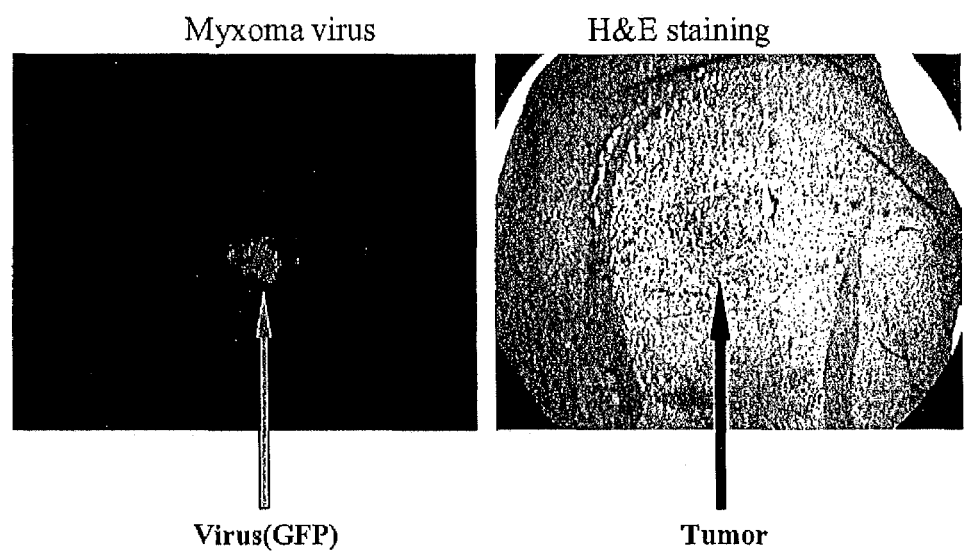
FIG. 16 is a fluorescent image and a photograph of a thin-sectioned mouse glioma infected with Myxoma virus expressing GFP showing that the Myxoma virus replicated only in tumour cells.

We studied the ability of MV to infect human tumour cells in an in vivo system. Nude mice were injected with human glioma cells, and subsequently developed intracranial gliomas. Live virus was able to infect these human tumours cells but did not infect surrounding cells (FIG. 15). The localization of fluorescent signal from GFP to the tumour is depicted in FIG. 16.

Given that many human tumours are non-responsive to interferon, and that the tumour cells do not have normal IFN signaling cascades compared to those found in normal human cells, studies were performed to investigate the effect of Myxoma virus on human tumours. The results are summarized below.

Figure 17:
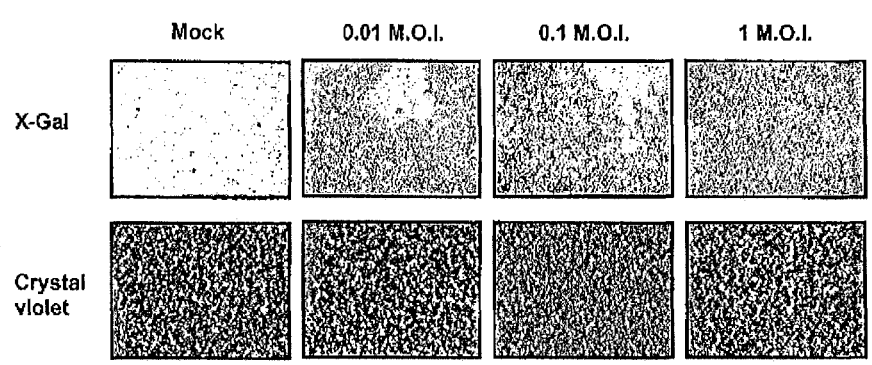
FIG. 17 is a phase contrast micrograph of HT29 human tumour cells, stained with either X-Gal or Crystal violet after infection with Myxoma virus, showing an example of a non-permissive infection in human cells.
Figure 18:
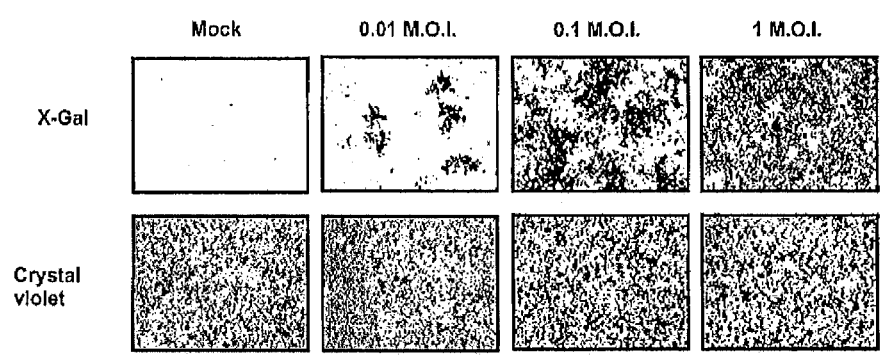
FIG. 18 is a phase contrast micrograph of HOP92 human tumour cells, stained with X-Gal or Crystal Violet after infection with Myxoma virus, showing an example of a permissive infection of human cells.
Figure 19:
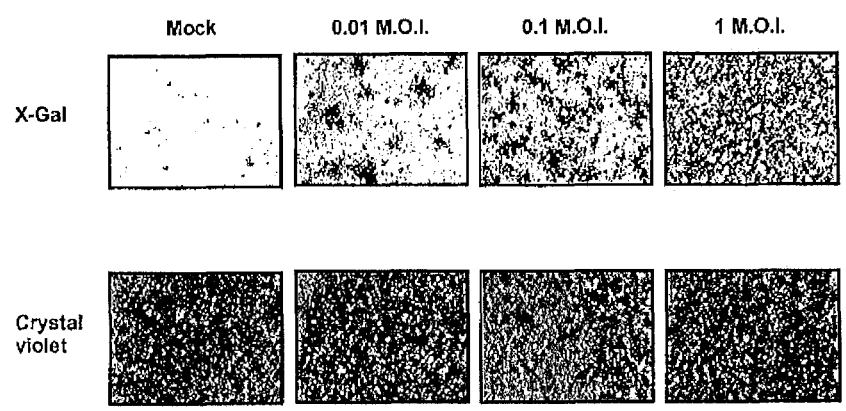
FIG. 19 is phase contrast micrograph of OVCAR4 human tumour cells, stained with either X-Gal or Crystal Violet after infection with Myxoma virus, showing an example of a permissive infection of human cells.
Figure 20:
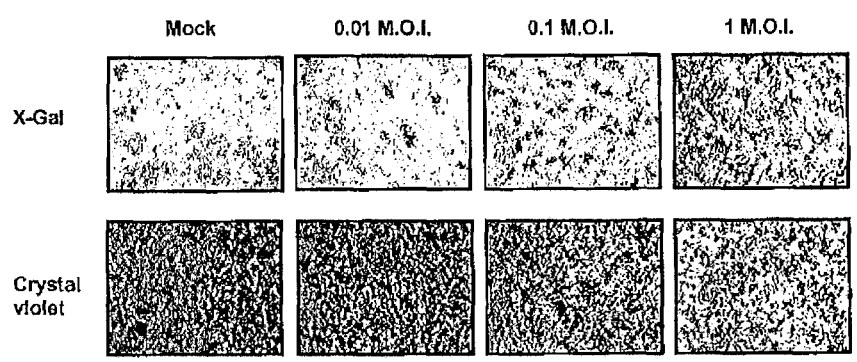
FIG. 20 is a phase contrast micrograph of SK-MEL3 human tumour cells, stained with either X-Gal or Crystal Violet after infection with Myxoma virus, showing an example of a permissive infection of human cells.
Figure 21:
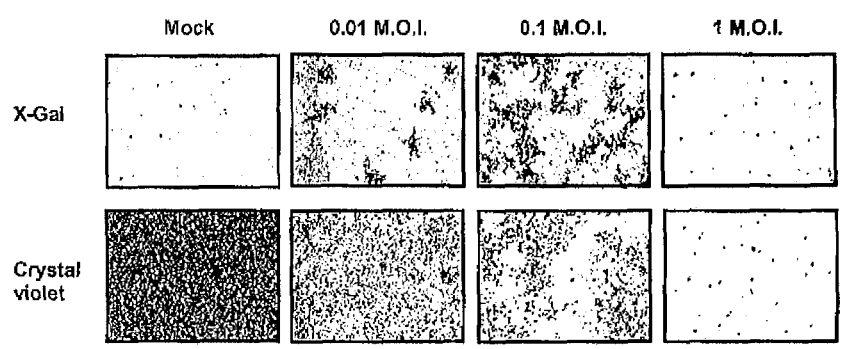
FIG. 21 is a phase contrast micrograph of SK-MEL28 human tumour cells, stained with either X-Gal or Crystal Violet after infection with Myxoma virus, showing an example of a semi-permissive infection of human tumour cells.
Figure 22:
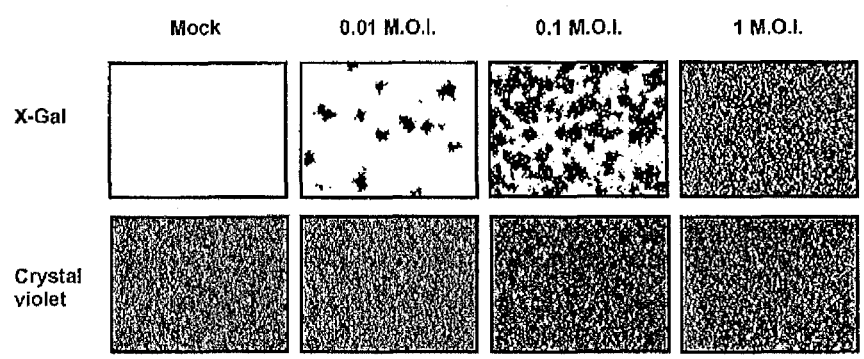
FIG. 22 is a phase contrast micrograph of BGMK cells, stained with either X-Gal or Crystal Violet after infection with Myxoma virus, showing a typical permissive control infection.

Initially, Myxoma virus was used to study the infectivity and cytolytic effects on various control and human tumour cell lines: BGMK, HT29, HOP92, OVCAR4, SK-MEL3, and SK-MEL28. MV demonstrated various infectivity and cytolytic results: HT29 (FIG. 17) HOP92 (FIG. 18), OVCAR4 (FIG. 19) SK-MEL3 (FIG. 20), SK-MEL28 (FIG. 21) and BGMK (FIG. 22).

Additional tumour cells were tested and Table 1 below classifies the various tumour types tested as permissive or non-permissive.

TABLE 1

Myxoma Virus Trophism for Human Tumour Cells

| Cell Line | Cell Origin | Species | Permissive | Non-Permissive |
|---|---|---|---|---|
| BGMK | Kidney | Monkey | X | |
| RK-13 | Kidney | Rabbit | X | |
| RL5 | T-Lymphocyte | Rabbit | X | |
| HOS | Osteosarcoma | Human | X | |
| PC3 | Prostate cancer | Human | X | |
| Caki-1 | Renal cancer | Human | X | |
| HCT116 | Colon cancer | Human | X | |
| 786-0 | Renal cancer | Human | X | |
| SK-OV-3 | Ovarian cancer | Human | X | |
| ACHN | Renal cancer | Human | X | |
| HOP92 | Lung cancer | Human | X | |
| SK-MEL3 | Melanoma | Human | X | |
| SK-MEL28 | Melanoma | Human | X | |
| OVCAR4 | Ovarian cancer | Human | X | |
| OVCAR5 | Ovarian cancer | Human | X | |
| DU145 | Prostate cancer | Human | X | |
| A498 | Renal cancer | Human | X | |
| T47D | Breast cancer | Human | X | |
| Colo205 | Colon cancer | Human | | X |
| HT29 | Colon cancer | Human | | X |
| MDAMB 435 | Breast cancer | Human | | X |
| M14 | Melanoma | Human | | X |
| MCF7 | Breast cancer | Human | | X |
| SK-MEL5 | Melanoma | Human | | X |

Figure 23:
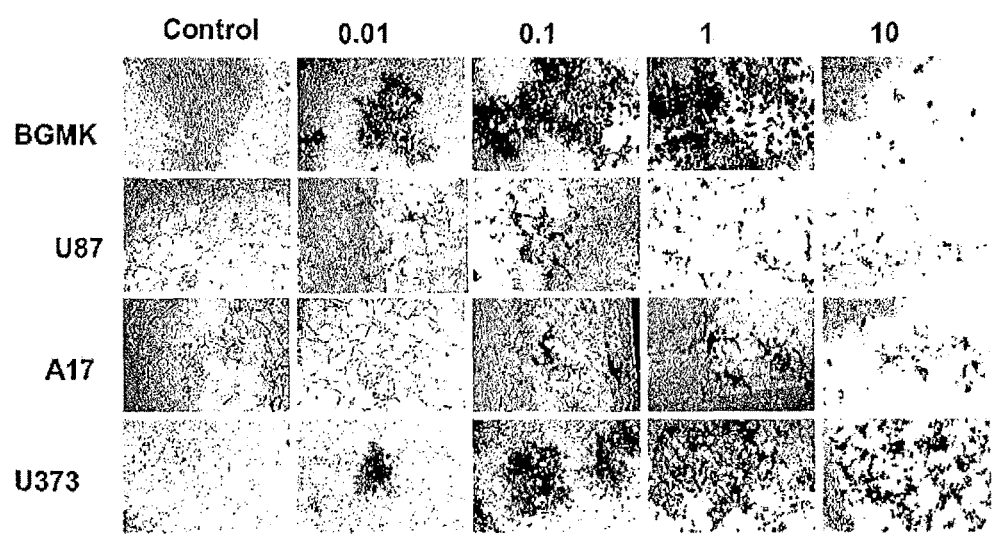
FIG. 23 is a phase contrast micrograph of positive control BGMK cells and human tumour lines U87, A172 and U373 infected with increasing concentrations of Myxoma virus expressing the LacZ protein, stained with X-Gal, showing that these human glioma cells were all permissive for Myxoma virus replication.
Figure 24:
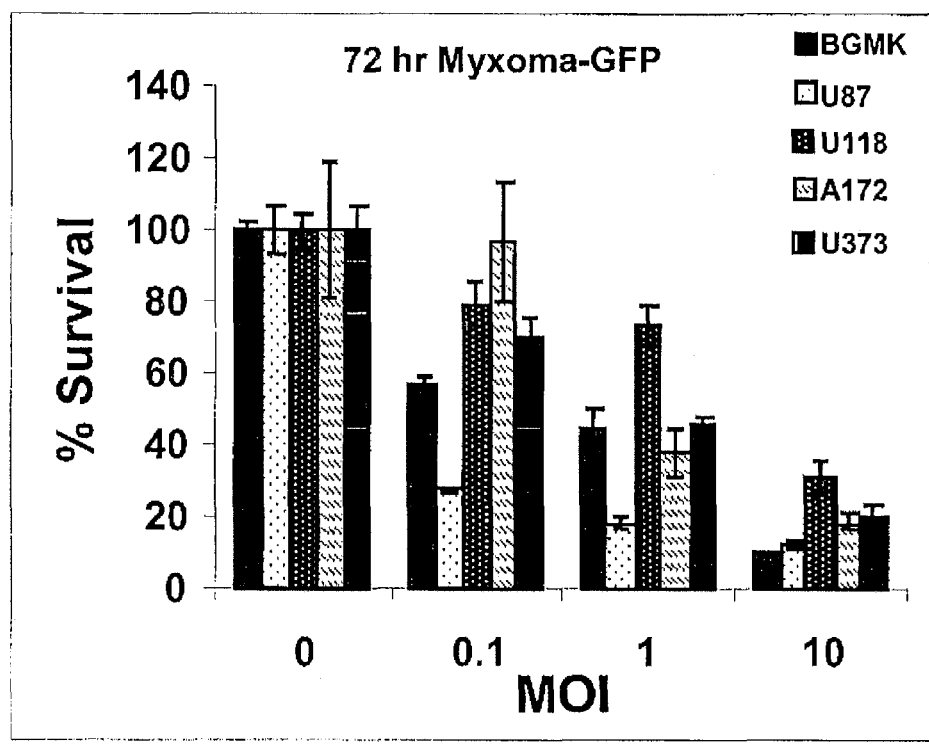
FIG. 24 is a graph depicting survival rate of BGMK, U87, A172 and U373 cells infected with Myxoma virus, 72 hours post-infection, at increasing concentrations of the virus, demonstrating the ability of Myxoma to kill all of these cells.
Figure 25:
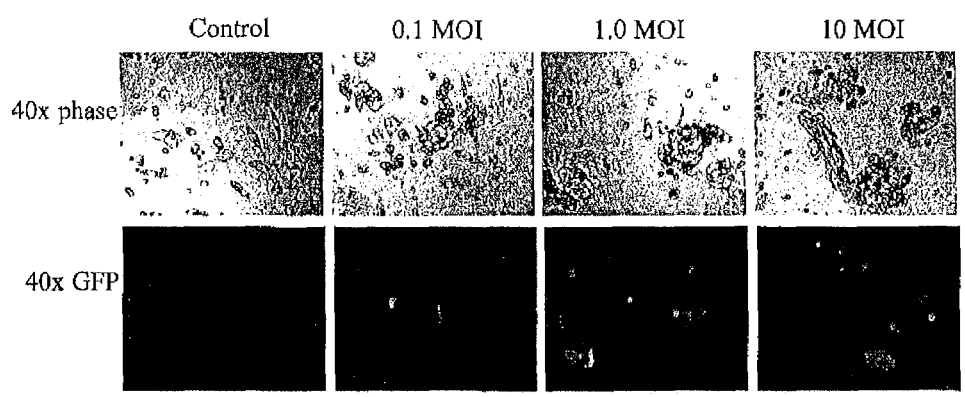
FIG. 25 is a phase contrast micrograph and fluorescence micrograph of SF04 1585 astrocytoma cells infected with MV GFP, showing the infection in primary human glioma cells.
Figure 26:
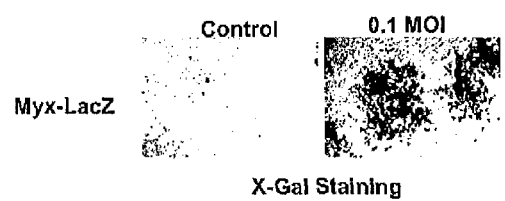
FIG. 26 is a phase contrast micrograph of U373 glioma cells infected with Myxoma virus expressing the LacZ protein and stained with X-Gal, showing infection of these human tumour cells.
Figure 27:
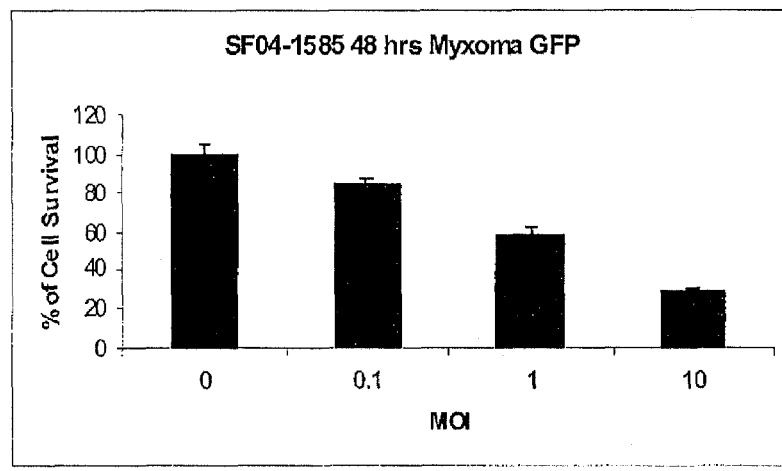
FIG. 27 is a graph depicting the survival rate of SF04 1585 cells infected with MV GFP 48 hours post-infection, showing killing of these infected human tumour cells.
Figure 28:
FIG. 28 is a fluorescence micrograph of Daoy and D384 medulloblastoma lines infected with Myxoma virus expressing GFP, showing infection of these human tumour cells.
Figure 28:

Various human tumour lines demonstrated varying responsiveness to infection with increasing concentrations of MV-LacZ. For example, U373 cells required higher virus titres to achieve the levels of cell killing achieved with lower virus titres in U87 (FIG. 23 and FIG. 24). Myxoma efficiently infected astrocytoma cells (FIG. 25), and glioma cells (FIG. 26). Myxoma was effective at 48 hours post-infection at killing human astrocytoma and pediatric medulloblastoma cells (FIGS. 27 and 28).

Example 2: Effect of Rapamycin on the Kinetics of Myxoma Virus Replication in Restrictive Cell Lines Virus Strains Viral strains used include wildtype MV ("vMyxLac"), and MV modified to have the MT-5 gene knocked out ("vMyxLacT5-"). Viruses were prepped and titred using standard techniques.

Cell Strains

Human experiments were performed on BGMK primate control cells, RK-13 rabbit control cells and normal human fibroblasts A9, restrictive human tumour cell lines 786-0 (renal), ACHN (renal), HCT116 (colon), MCF-7 (breast), MDA-MB-435 (breast), M14 (melanoma) and COLO205 (colon).

Methods

Generally, assays and experiments were performed as described in Lalani et al. *Virology* (1999) 256: 233-245; Johnston et al. *J Virology* (2003) 77(13): 7682-7688; and Sypula et al. *Gen Ther Mol Biol* (2004) 8: 103.

For viral growth curves, cells were grown in vitro in a monolayer, and pretreated with 20 nM rapamycin or a control (1:5000 dilution of DMSO) prior to infection with virus.

Samples of indicated cell lines infected with the indicated viral strain were collected at 72 hours post infection and lysed. The virus contained within the cell lysates was titrated and used to infect BGMK monolayers. At 48 hours post infection, cells were fixed and stained using X-gal.

Results

Myxoma virus has been previously demonstrated by the inventors to be able to infect and replicate in many types of human tumor cells (Sypula et al. (2004) *Gene Ther. Mol. Biol.* 8:103). This rabbit specific virus can preferentially infect a majority (approximately 70%) of human cancer cell lines from the NCI reference collection. In addition, the host range gene M-T5 was found to play a critical role during Myxoma virus infection of many of these cell lines.

In the present investigation of potential intracellular molecules that may be affecting the ability of Myxoma to selectively replicate within human tumour cells, the effect of rapamycin was tested.

Figure 29:
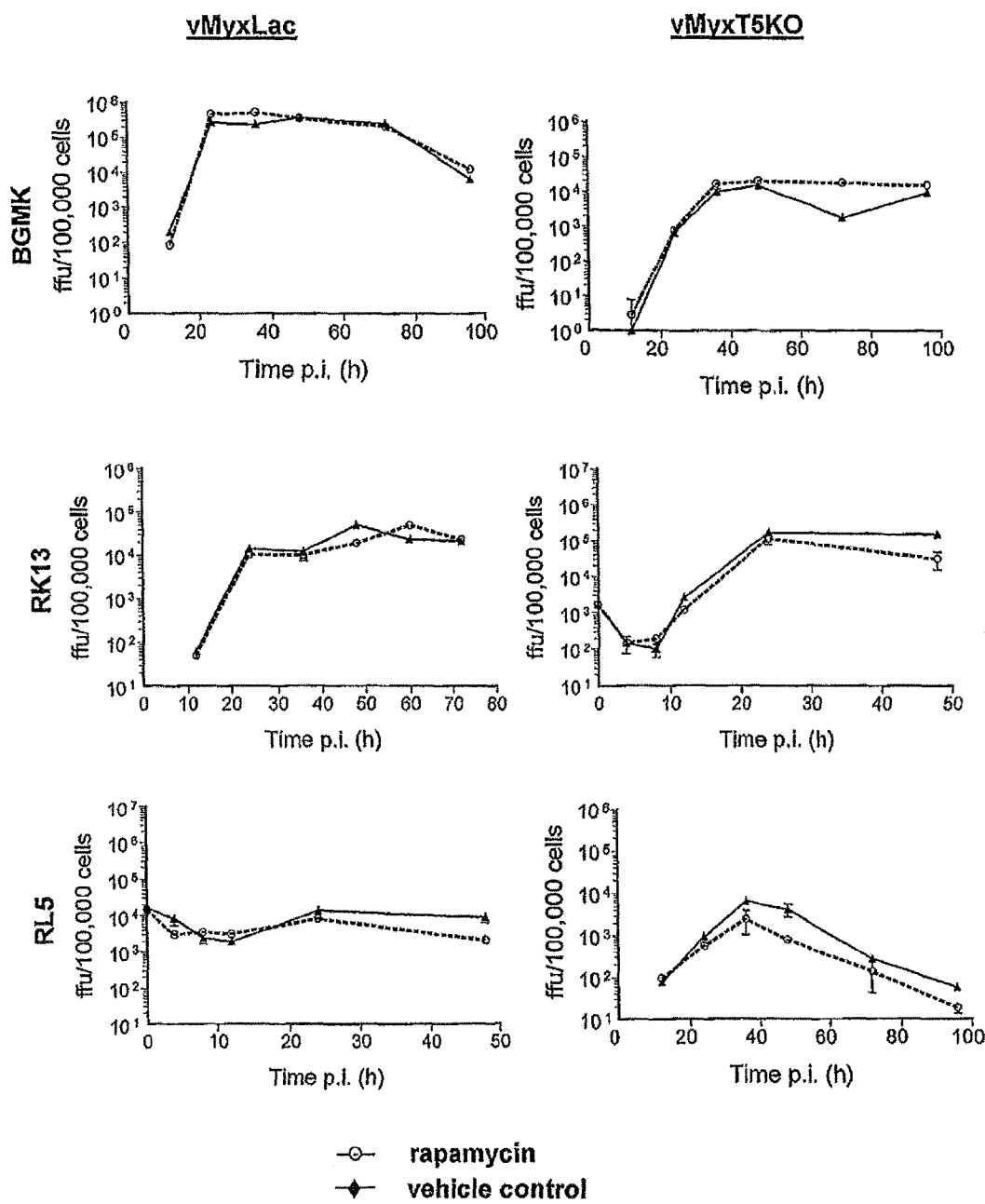
FIG. 29 is graphical representations of the rate of virus production in various cell lines with or without pre-treatment with rapamycin: BGMK (primate control cell line); RK-13 and RL5 (rabbit control cell lines); 4T1 and B16F10 (mouse cancer cell lines); HOS, PC3, 786-0, HCT116, ACHN, MCF-7, M14 and COLO205 (human cancer cell lines); using wildtype virus vMyxLac and the M-T5 knock out virus vMyxT5KO as indicated.
Figure 29:
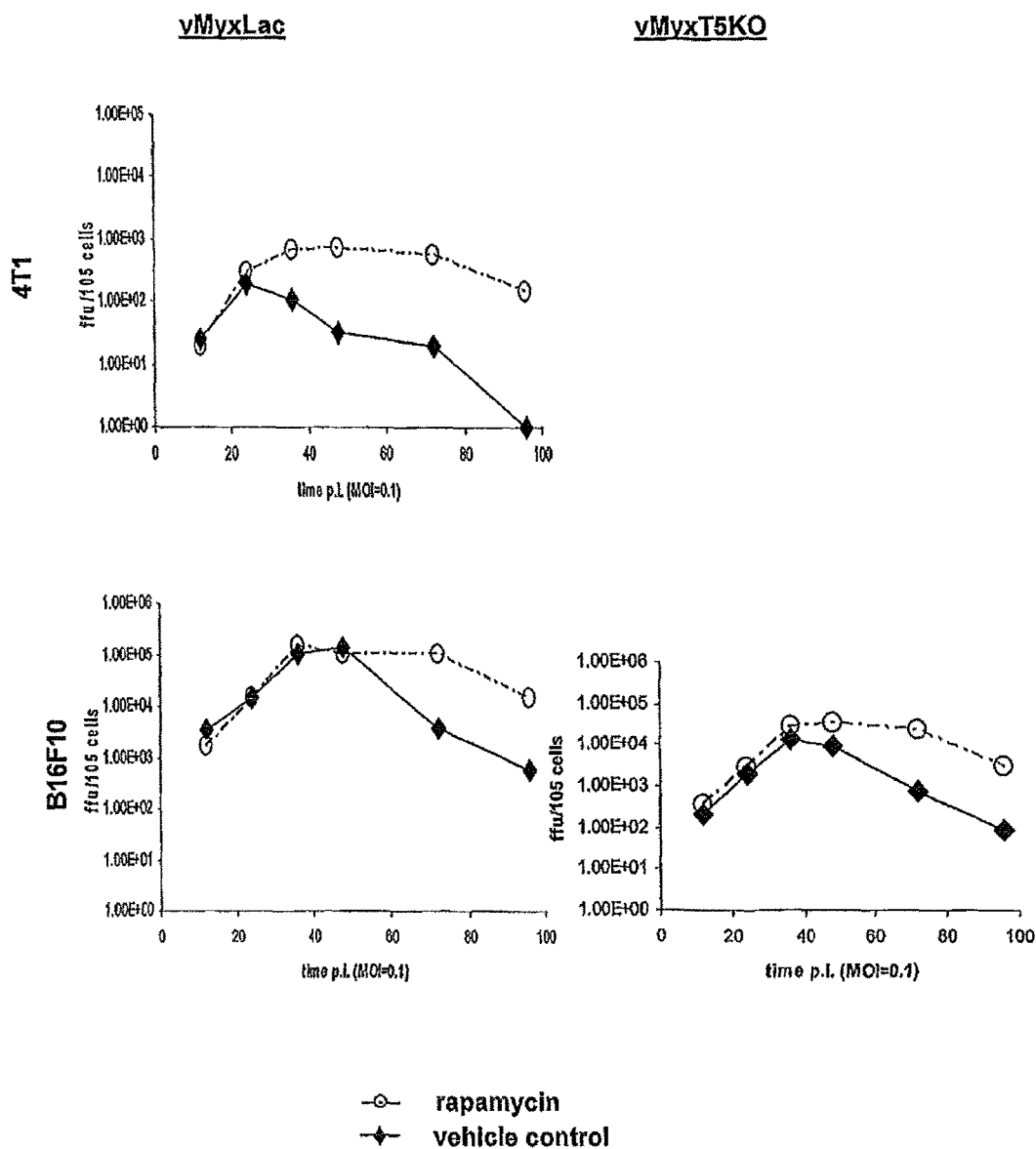
Figure 29:
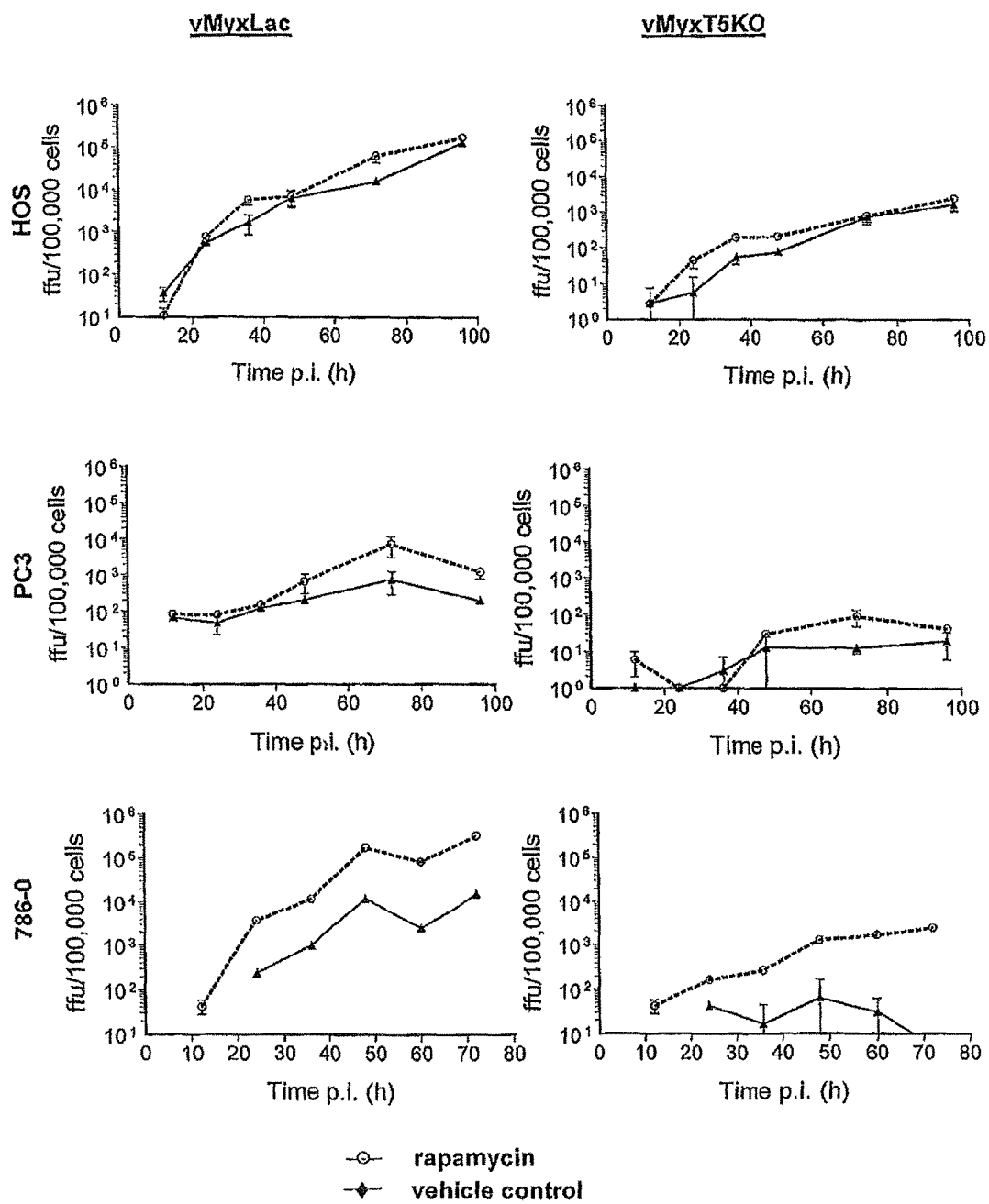
Figure 29:
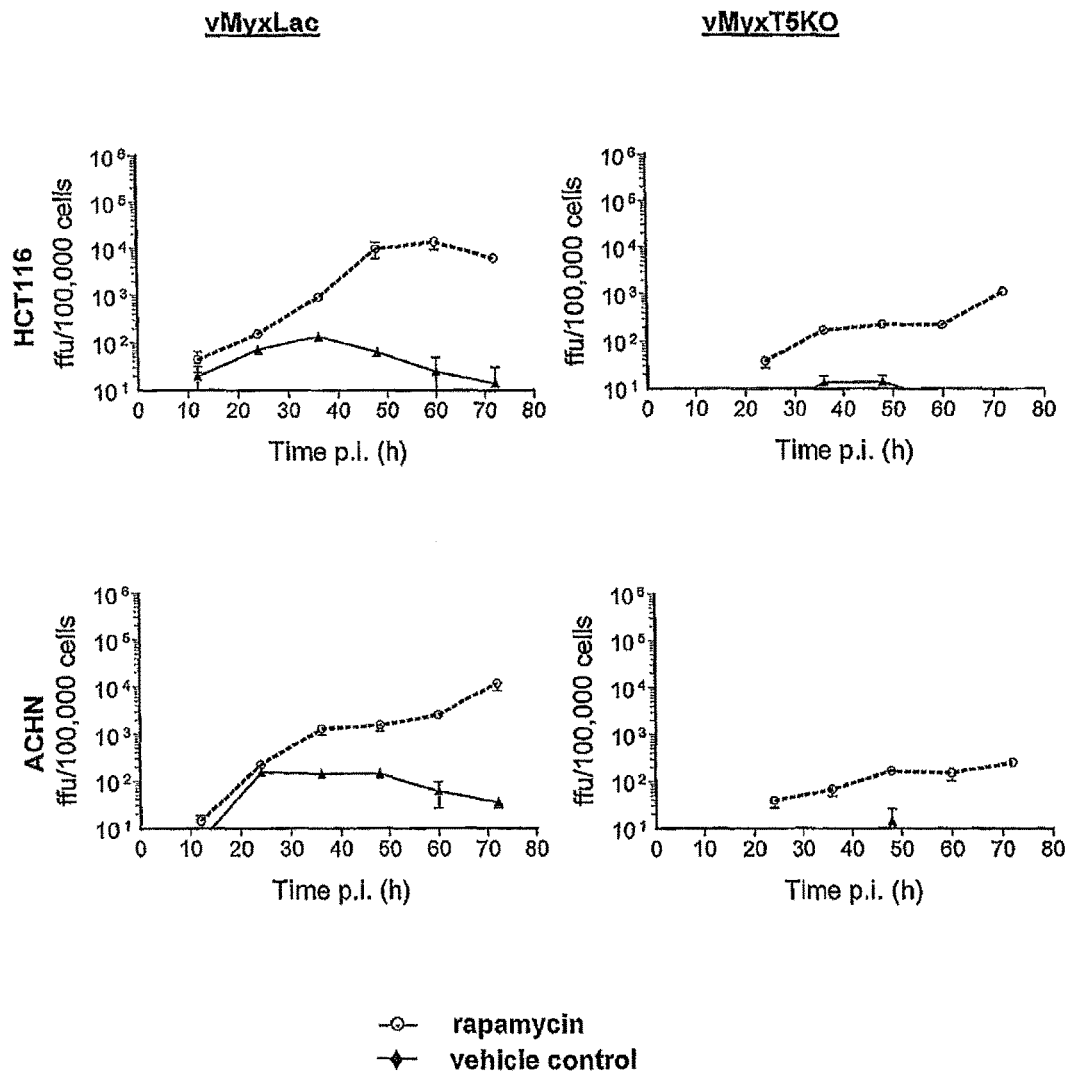
Figure 29:
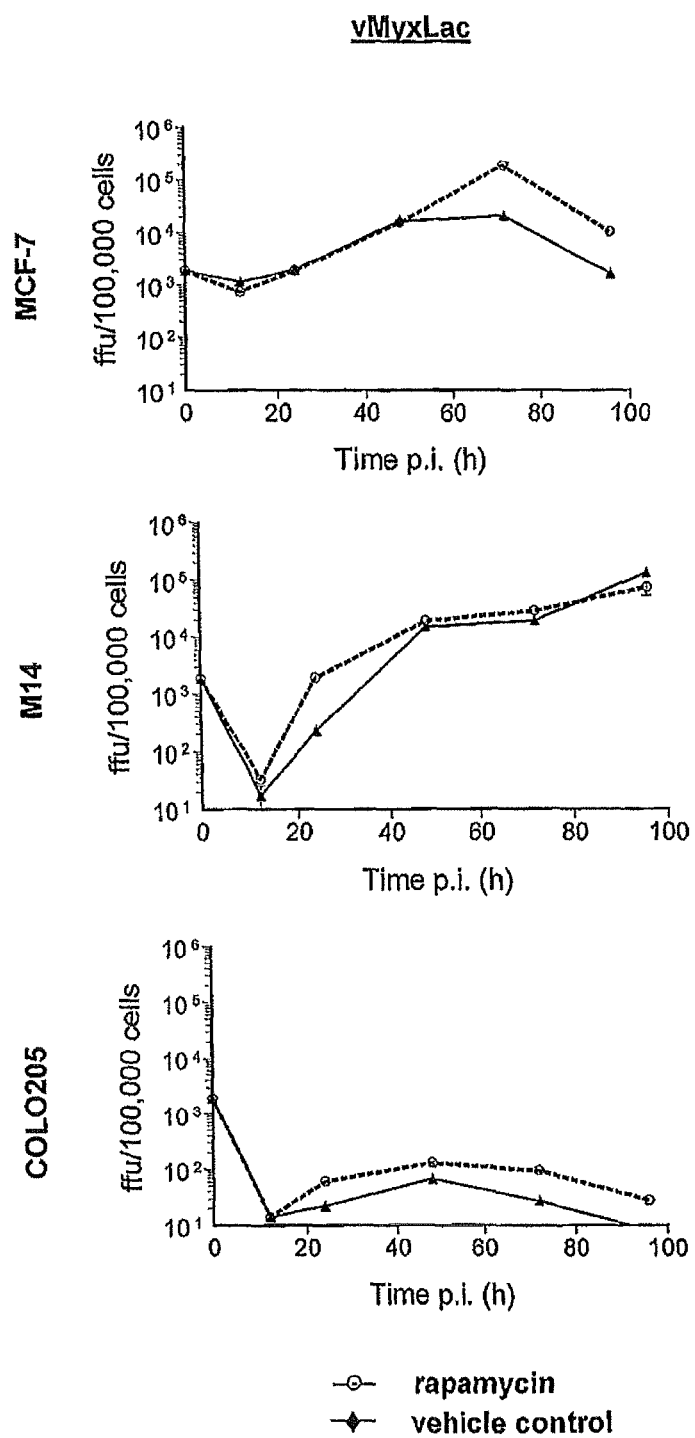

As seen in FIG. 29, the ability of Myxoma virus to replicate and spread following a low multiplicity of infection (MOI) was performed using a multistep growth curve, using BGMK (control primate cell line); RK-13 and RL5 (control rabbit cell lines); 4T1 and B16F10 (mouse cancer cell lines); HOS and PC3 (permissive human cancer cell lines); 786-0, HCT116 and ACHN (restrictive human cancer cell lines); MCF-7, M14 and COLO205 (abortive human cancer cell lines). Both wild type vMyxLac and the M-T5 knock out virus vMyxT5KO were tested to investigate the ability of both viruses to infect and spread throughout the monolayer in the presence and absence of pre-treatment with rapamycin. Virus titre was assessed by foci formation on BGMK cells. Cells were pretreated with 20 nM rapamycin or appropriate vehicle control (1:5000 dilution of DMSO) for 6 hours before infection.

As demonstrated, rapamycin has no effect on control BGMK cells, nor on either of the rabbit cell lines tested, including the RL-5 cells, which are non permissive for the MT-5 knock out virus. However, rapamycin does enhance the replication of myxoma virus in mouse tumour cell lines, and marginally in permissive (Type I) cell lines, such as PC-3. Rapamycin has less of an effect on highly permissive cells such as HOS cells, likely due to the fact that such cell lines are already maximally permissive for the Myxoma virus. The greatest effect with rapamycin was observed in the restrictive (Type II) cell lines (786-0, HCT116 and ACHN), which are permissive for wildtype virus but non-permissive for the vMyxT5KO strain. Some effect was seen even in abortive (Type III) cell lines MCF-7 and COLO205, although not in abortive cell line M14.

Figure 30:
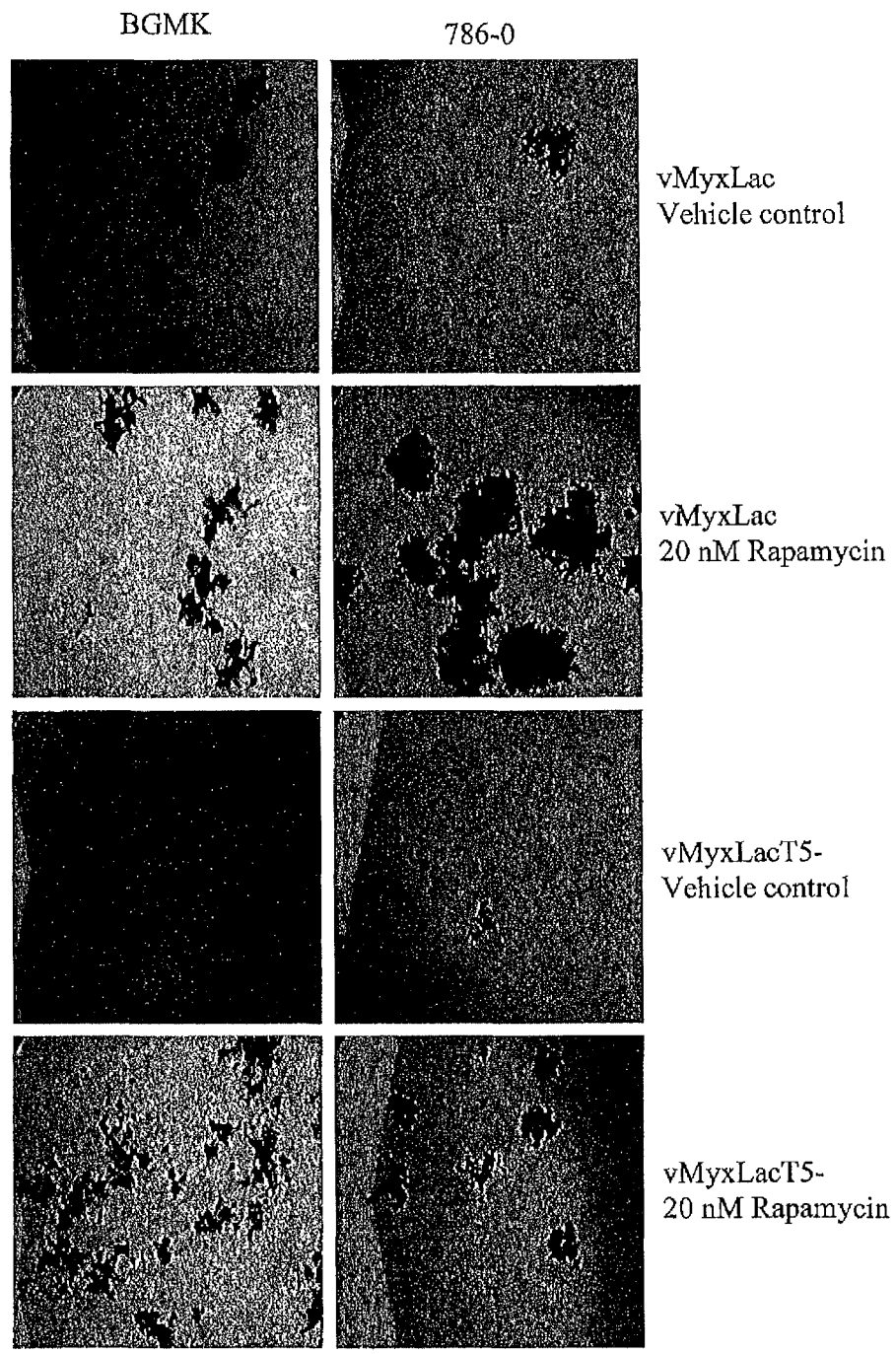
FIG. 30 is photographs of virally infected cell lines, infected with either vMyxLac or vMyxLacT5-.

Samples of the BGMK and 786-0 infected cells were then collected and lysed, and the isolated virus was used to infect monolayers of BGMK cells (FIG. 30). Virally infected cells were visualized using X-Gal staining.

Pretreatment of tumour cells that are "restrictive" for Myxoma infection, i.e. those cells that permit the replication of the wild type Myxoma virus but not the MT-5 knock-out virus, with rapamycin resulted in a restoration of the ability of Myxoma virus to replicate in these cancer cell lines, which include renal, colon and ovarian cancer cell lines (FIGS. 29 and 30).

In addition, the treatment with rapamycin enhanced the ability of the wild type virus to replicate in these same cells, but not control rabbit or primate cells. These results indicate that rapamycin acts to enhance Myxoma virus infection. In addition, rapamycin appears to influence the ability of cancer cells that are poorly infectable by this virus to permit virus replication.

Figure 31:
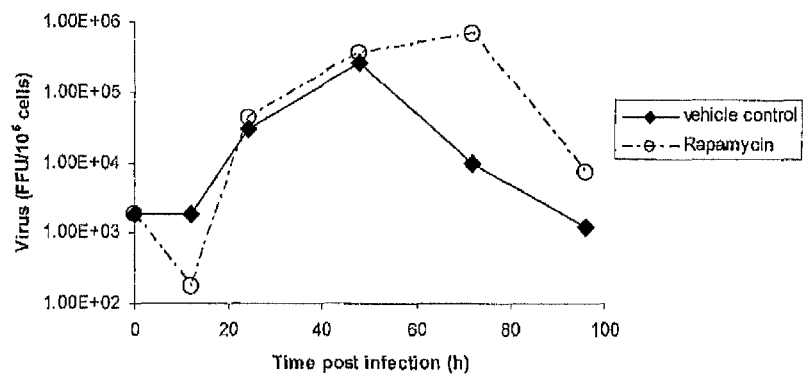
FIG. 31 is graphical representations of the rate of virus production in various cell lines (BGMK; A9; MCF-7; MDA-MB-435; M14; and COLO205) with or without pre-treatment with rapamycin.
Figure 31:
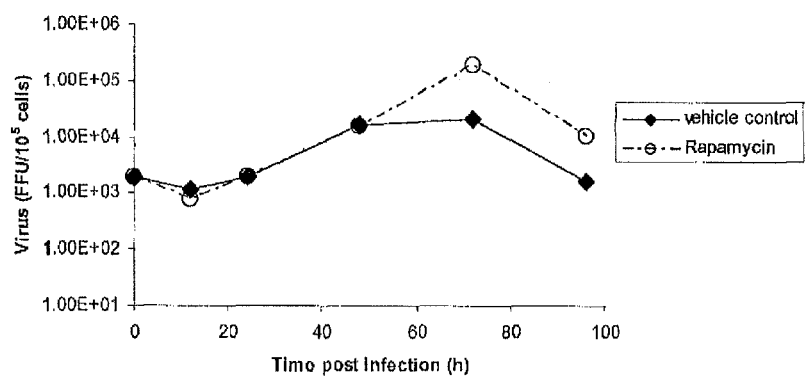
Figure 31:
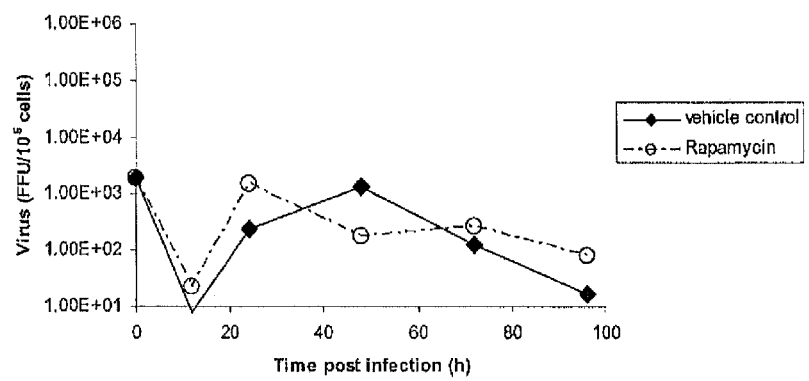
Figure 31:
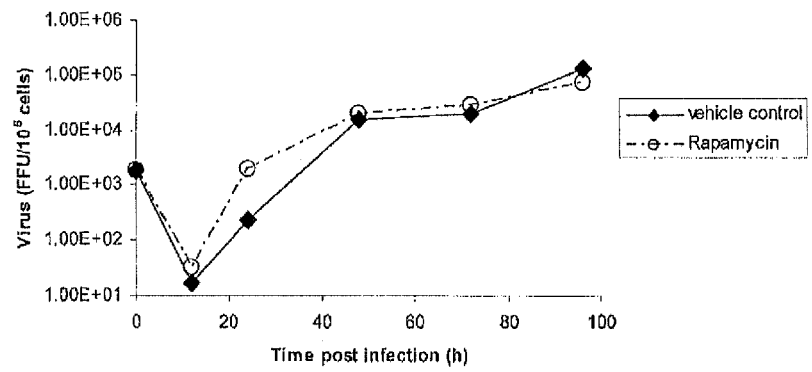
Figure 31:
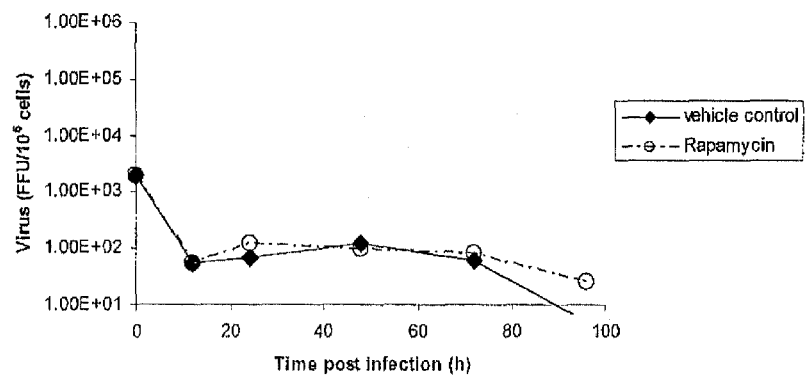
Figure 31:
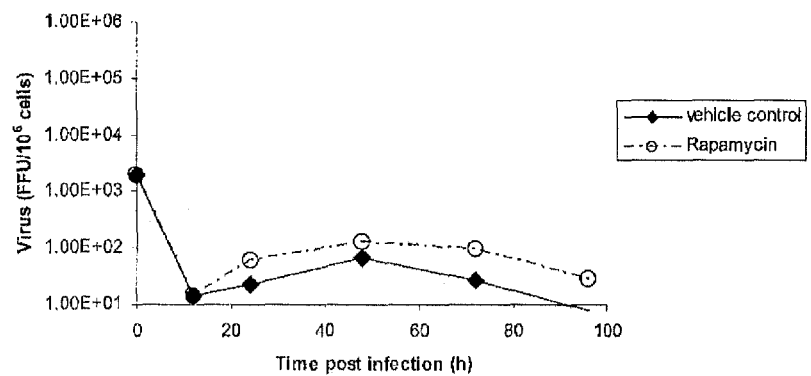

Subsequent experiments examined the effect of rapamycin treatment on human tumour cells that could not support wild type Myxoma virus infection (FIG. 31). The pretreatment had little effect on control primate cells or normal human fibroblasts, yet could enhance virus infectivity in several cell lines, including the breast cancer cell line MCF-7. As several of the human tumour cell lines remained resistant to rapamycin treatment, as well as the control cell lines, it is unlikely that rapamycin treatment could permit Myxoma virus to productively infect non-transformed tissue.

Example 3: Myxoma Virus M135KO Variant as an Improved Oncolytic Virus Candidate

M135R is Expressed from Myxoma Virus as an Early Gene

Figure 32:
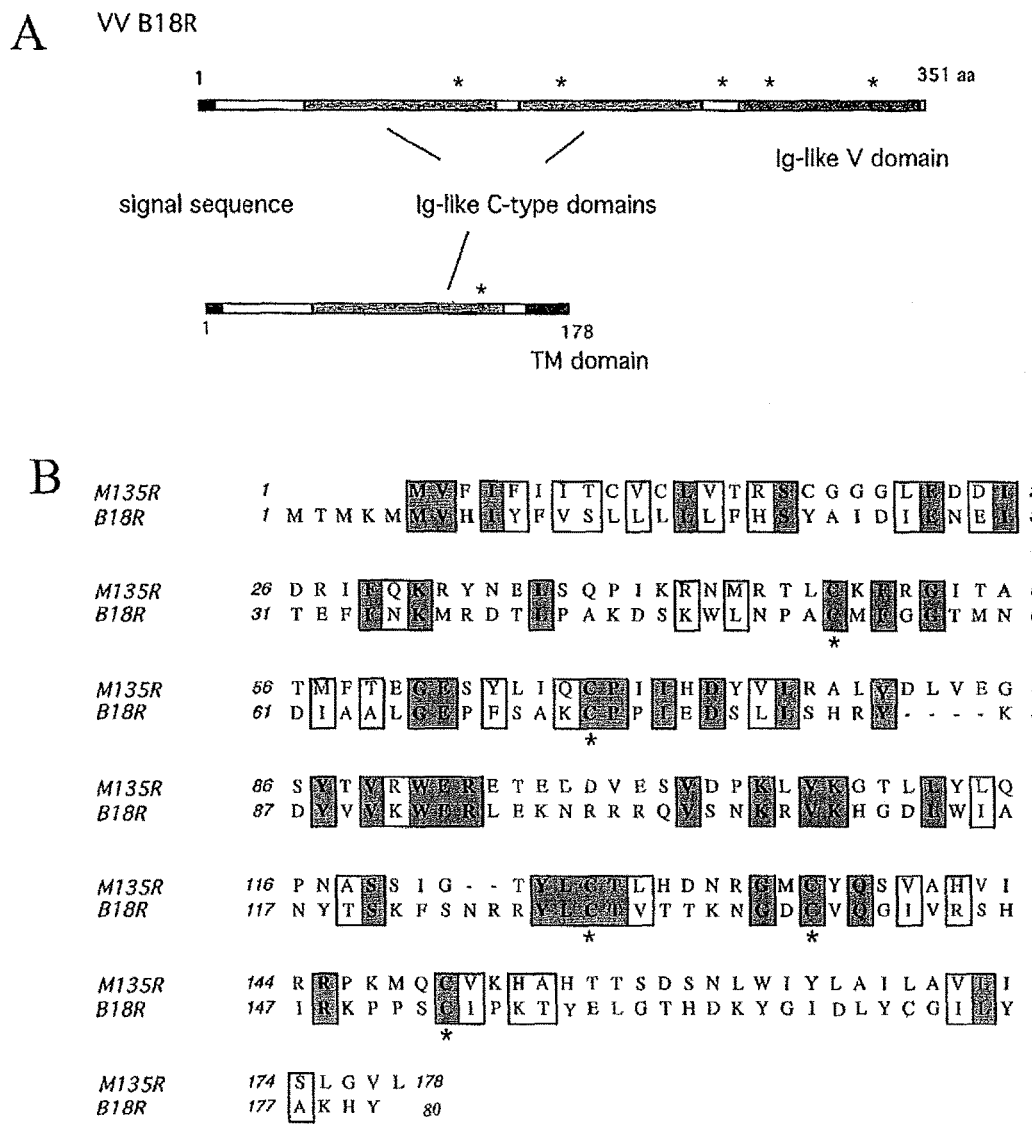
FIG. 32 is (A) a schematic alignment of Myxoma virus protein M135R and Vaccinia virus protein B18R and (B) an amino acid sequence alignment between M135R and the first 179 amino acids of B18R.

Myxoma virus encodes a protein (M135R) identified from the sequencing of the MV genome (Cameron et al. Virology (1999) 264: 298-318) predicted to mimic the host IFNα/β receptor and prevent IFNα/β from triggering a host anti-viral response (Barrett et al. Seminars in Immunology (2001) 13:73-84). This prediction is based on sequence homology to the viral IFNαβ receptor homolog from vaccinia virus (B18R), which virus has been demonstrated to employ such an immune evasion strategy (Symons et al. Cell (1995) 81:551-560). However M135R is only half the size of VV B18R and all other IFN α/β-R homologs sequenced from poxviruses, and in all cases aligns only to the amino terminus half of poxviral IFN α/β-R homologs. FIG. 32 indicates the predicted structure and sequence similarity between M135R from MV and B 18R from VV. Only the first 179 amino acid residues of B18R are shown in the sequence alignment. Table 2 indicates the % identity between M135R and the indicated poxviral IFN α/β-R homologs. Numbers above the diagonal represent % identity and numbers below the diagonal represent % similarity between any two species. The numbers in brackets across the top represent the number of amino acids in the putative proteins. Comparison was done between the predicted full length copy of M135R (178 amino acids) and the first 178 residues of each homolog only.

TABLE 2

Comparison of M135R to Other Poxviral Homologs
% Identity

| species | Myxoma (178) | Vaccinia (351) | Variola (354) | Monkeypox (352) | Cowpox (351) | Ectromelia (358) | Camelpox (355) | YLDV (351) | Swinepox (344) | LSDV (360) |
|---|---|---|---|---|---|---|---|---|---|---|
| Myxoma | — | 24 | 21 | 24 | 23 | 21 | 22 | 20 | 18 | 17 |
| Vaccinia | 39 | — | 80 | 93 | 90 | 84 | 79 | 20 | 23 | 25 |
| Variola | 36 | 88 | — | 79 | 87 | 88 | 79 | 19 | 24 | 24 |
| Monkeypox | 38 | 95 | 87 | — | 86 | 83 | 78 | 20 | 20 | 26 |
| Cowpox | 38 | 93 | 93 | 91 | — | 92 | 88 | 21 | 23 | 25 |
| Ectromelia | 35 | 89 | 93 | 87 | 94 | — | 87 | 17 | 21 | 25 |
| Camelpox | 34 | 86 | 94 | 85 | 92 | 93 | — | 17 | 23 | 24 |
| YLDV | 38 | 37 | 37 | 37 | 38 | 34 | 34 | — | 23 | 28 |
| Swinepox | 32 | 39 | 39 | 36 | 39 | 35 | 37 | 38 | — | 25 |
| LSDV | 32 | 39 | 39 | 41 | 38 | 39 | 36 | 43 | 38 | — |

Figure 33:
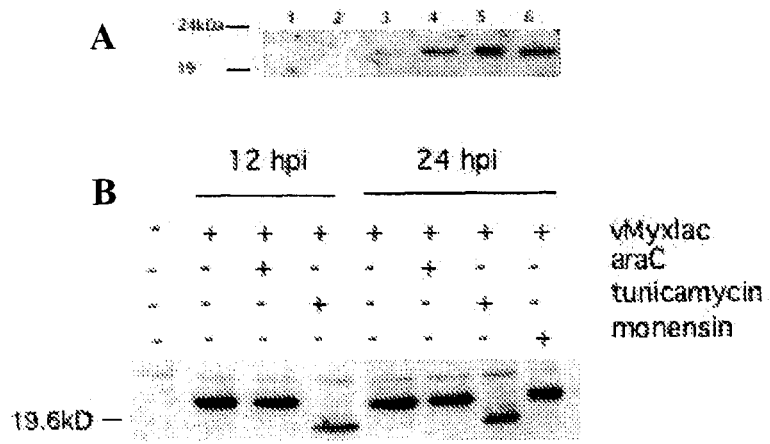
FIG. 33 is (A) a Western blot of M135R expressed in BGMK cells infected with Myxoma virus Lausanne (vMyxLau) and (B) a Western blot of M135R expressed in BGMK cells infected with vMyxLau and treated with araC, tunicamycin or monensin.

Peptides against predicted immunogenic regions of M135R were synthesized and used to generate polyclonal antibodies in rabbits that were used in western blot analysis, immunoprecipitations and immuno-fluorescence. Immunoblotting confirmed that M135R is synthesized as an early gene whose expression can be detected as early as three hours post infection (FIG. 33A; lane 1: mock infected BGMK cells; lanes 2-6: BGMK cells infected with vMyx-Lau 0, 3, 6, 18 and 36 hours post infection, respectively). Treatment of infected cells with AraC indicates that synthesis of M135R was not altered by inhibition of late protein expression and is therefore an early gene (FIG. 33B). However treatment with tunicamycin indicates that M135R is N-linked glycosylated, likely at the single site predicted from the sequence (FIG. 33B). Monensin treatment suggests that there is no O-linked glycosylation. For the results shown in FIG. 33, BGMKs were infected at an moi of 10 with Myxoma virus. Cells were treated with AraC at a concentration of 40 µg/ml, tunicamycin at 1 µg/ml and monensin at 1 µg/ml, or were untreated, at the times indicated. M135R was detected with a peptide antibody.

M135R Encodes a Signal Sequence but is not Secreted

Sequence analysis of M135R indicates the presence of a predicted signal sequence (FIG. 32B). However there is also a predicted transmembrane domain at the carboxy terminus (FIG. 32B). Immunoblots of supernatants from infected BGMK cells indicate that M135R is not secreted. However, M135R is easily detected in whole cell lysates (FIG. 33). To test whether the signal sequence functioned to drive M135R to the cell surface, we deleted the transmembrane domain and cloned the mutant into a baculovirus expression system.

Comparison of AcM135R and Ac135ΔTM infected supernatants indicated that full length M135R is found in the cell lysate there is no evidence of secretion. In contrast Ac135ΔTM is secreted and confirms that the signal sequence functions to drive M135R into the extracellular environment (data not shown).

M135R Protein Localizes to the Surface of Infected Cells

Figure 34:
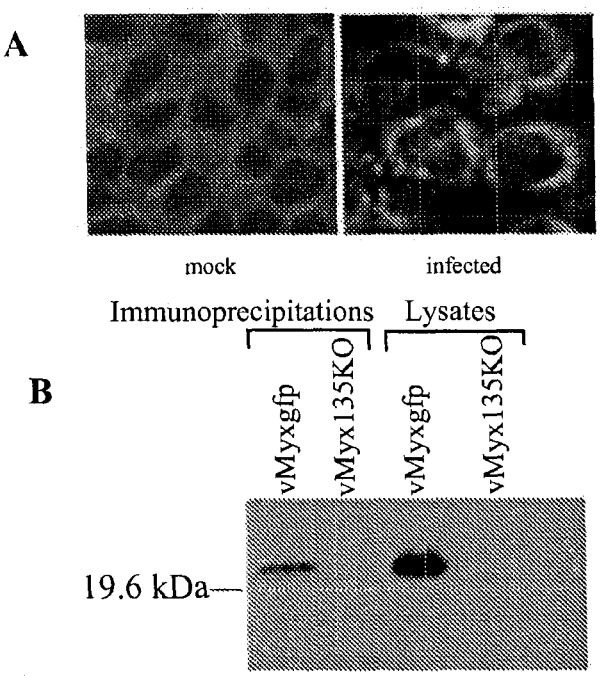
FIG. 34 is (A) a fluorescence micrograph of BGMK cells mock infected or infected with Myxoma virus and stained for M135R and (B) a Western blot against immunoprecipitations or cell lysates of cells infected with wildtype Myxoma virus (vMyxgfp) or an M135R knockout strain (vMyx135KO) using anti-M135R antibody.

The observation that M135R has a functional signal sequence as well as a transmembrane domain prompted us to test the localization of M135R. Two pieces of evidence indicate that M135R localizes to the cell surface. First, when BGMKs were seeded onto glass coverslips and infected with vMyxLau (moi of 10) for 24 hours then M135R was detected by immunostaining with affinity purified anti-M135R followed by FITC-conjugated secondary antibody (FIG. 34A). M135R staining pattern indicates localization to the cell surface of infected cells. vMyxLau is a true wildtype strain of Myxoma virus which has not been altered by insertion of the β-gal or EGFP gene.

The second piece of evidence for cell surface localization M135R follows biotinylation of cell surface proteins of GHOST cells infected with either vMyxgfp or vMyx135KO. Twenty-four hours post infection cell lysates were prepared. Streptavidin agarose beads were mixed with 500 μg of total cellular protein from cell lysates for 45 minutes. The beads were washed and separated on a 15% PAGE-SDS gel and then probed with anti-M135R. 50 μg of total protein from the infected cell lysates were run as controls. Immunoprecipitation of biotinylated surface proteins indicates that m135R is at the surface of infected cells (FIG. 34B).

M135R is Non-Essential for Myxoma Virus Replication In Vitro

Figure 35:
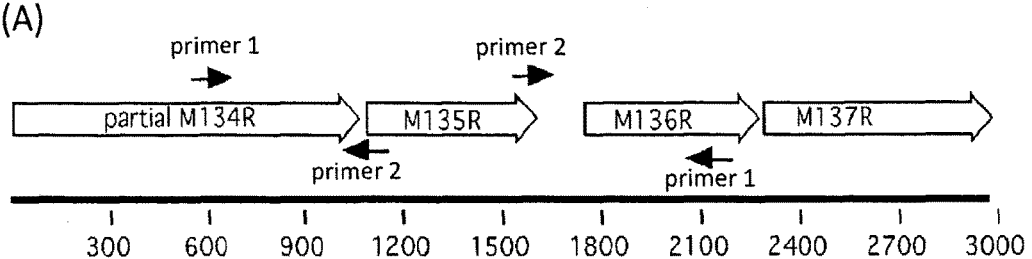
FIG. 35 is (A) is a schematic diagram of the cloning strategy to produce vMyx135KO, (B) an agarose gel of the PCR insert product and (C) a Western blot of cells infected with wildtype and M135R knockout Myxoma virus.
Figure 35:
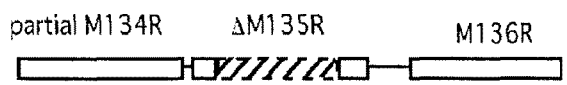
Figure 35:
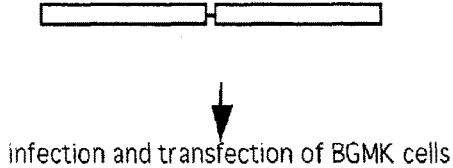
Figure 35:
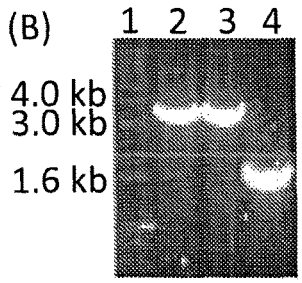
Figure 35:
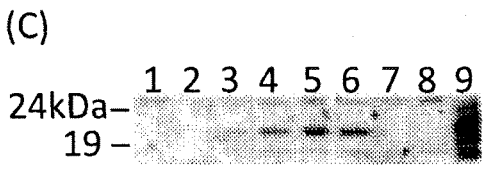

To test the ability of M135R to act as a virulence factor we constructed a recombinant virus in which M135R was deleted and replaced by a cassette encoding EGFP and gpt under VV early/late promoters (460 nucleotides, or 86% of the orf was deleted). The cloning strategy and cassette is shown in FIG. 35A. The recombinant was plaque-purified by selecting virus clones expressing EGFP. The purity of the recombinant was confirmed by PCR (FIG. 35B; Lane 1 is the 1 Kb plus DNA ladder, Lane 2 and 3 are PCR products from two purified vMyx135KO clones. The PCR product represents the region into which the M135R coding region has been deleted and the EGFP/gpt marker has been inserted. Lane 2 is plaque 1 and Lane 3 is plaque 2. Lane 4 represents the same region and covers the native, uninterrupted M135R locus.). Immunoblotting of BGMK cells infected with either vMyxLau or vMyx135KO confirmed that vMyx135KO had lost M135R expression (FIG. 35C; time course of expression of M135R: Lane 1 is uninfected BGMK cells. Lanes 2-6 represent BGMK cells infected with vMyxLau at times 0 (lane 2), 3 (lane 3), 6 (lane 4), 18 (lane 5), and 36 hours post infection (lane 6). Lanes 7 and 8 represent BGMK cells infected with vMyx135KO at 6 (lane 7) and 18 (lane 8) hours post infection. Lane 9 is a positive control with M135R expressed in AcNPV.).

Figure 36:
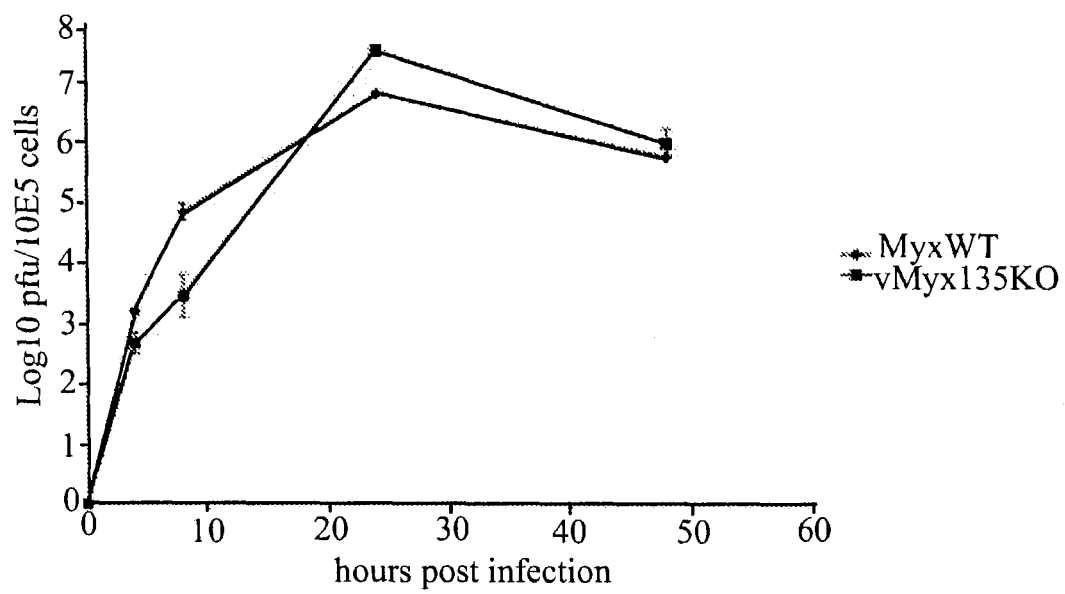
FIG. 36 is a growth curve of viral foci in BGMK cells infected with vMyxgfp or vMyx135KO.

Single step growth curves were used to test the ability of vMyx135KO to replicate in BGMK cells. BGMK cells were infected with vMyxgfp or vMyx135KO at an moi of 5 and cells were collected at the times indicated. Virus titres were determined on BGMK cells. There was no difference in the replication pattern between vMyxgfp and vMyx135KO (FIG. 36). These results indicate that M135R is not required for replication in vitro.

Figure 37:
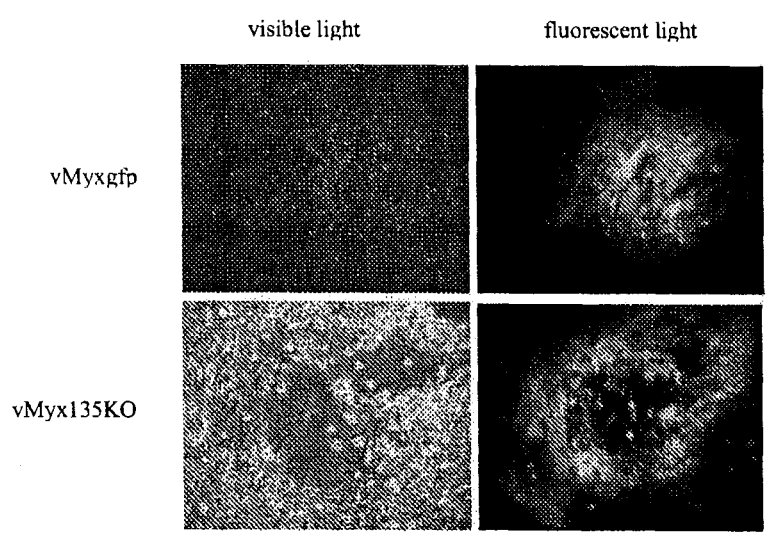
FIG. 37 is light and fluorescent micrographs of rabbit embryo fibroblasts infected with vMyxgfp or vMyx135KO.
Figure 38:
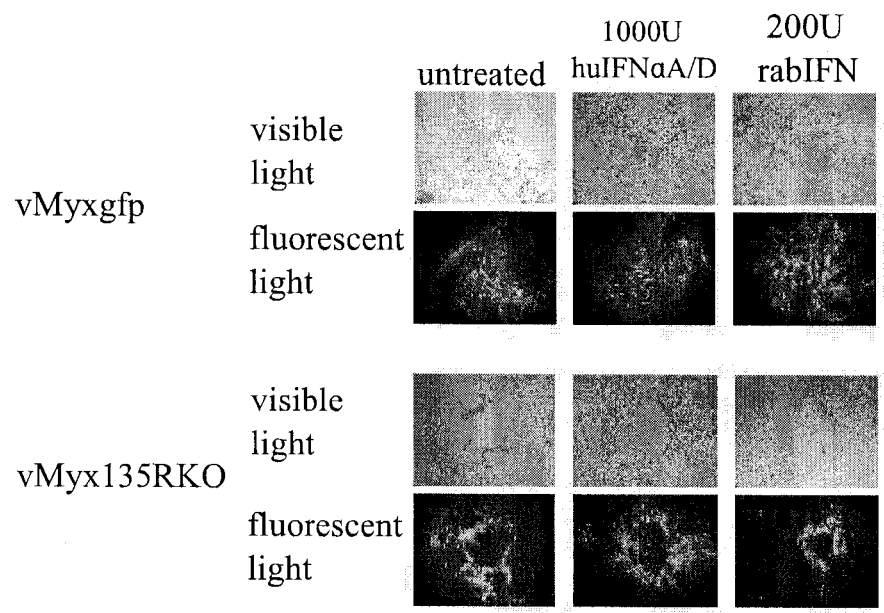
FIG. 38 is light and fluorescent micrographs of rabbit HIG82 fibroblasts infected with vMyxgfp or vMyx135KO.
Figure 39:
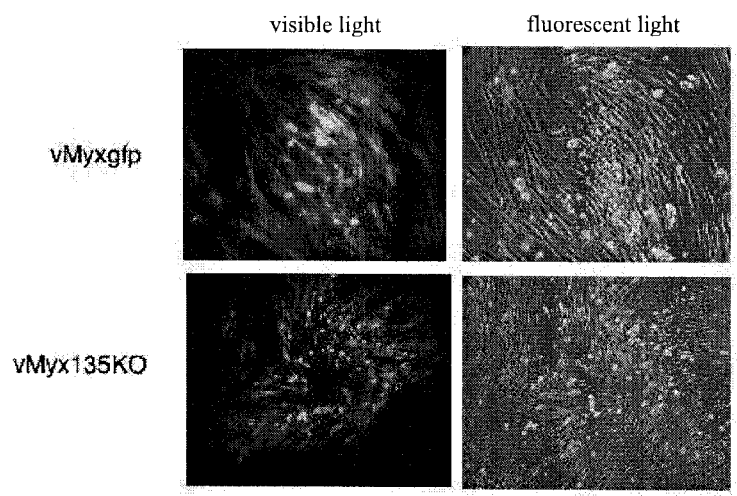
FIG. 39 is light and fluorescent micrographs of human primary fibroblasts infected with vMyxgfp or vMyx135KO.

During our studies of the ability of another gene of Myxoma to influence Myxoma replication in rabbit primary embryo fibroblasts (REFs), we used vMyx135KO as a knockout control and observed a curious phenomenon. Infection of the REFs with vMyxgfp resulted in a normal focus of infection however vMyx135KO produced a plaque-like zone of infection (FIG. 37). When we tested other cells to confirm this phenotype we were able to replicate the plaque formation in other rabbit fibroblasts (HIG-82, FIG. 38) and human primary fibroblasts (ccd922-sk, FIG. 39).

M135R is a Critical Virulence Factor for Pathogenesis in Rabbits

We next tested the ability of vMyx135KO to produce myxomatosis in lab rabbits. In contrast to the animals injected with vMyxLau or vMyxgfp which developed normal myxomatosis and had to be euthanized between days 9 and 10 post injection, the rabbits injected with vMyx135KO recovered completely (Table 3). To confirm that loss of M135R caused the attenuation of vMyx135KO we generated a revertant virus in which M135R was restored and we tested the ability of this revertant (vMyx135REV) to restore the ability to produce myxomatosis. All four treated groups of rabbits responded in a similar manner for the first six days following injection of the respective viruses (Table 3). We observed a large, red, raised lesion at the site of injection in all treatment groups by 4 days post infection. However beginning at day 6 and continuing over the next 3-4 days the differences between the different viruses became evident. Those animals injected with the wildtype or revertant virus had numerous secondary lesions in the ears, eyes and nose which were not observed in the animals injected with vMyx135KO (Table 3). We conclude that loss of M135R drastically attenuated MV in animal models and indicates that M135R is a critical virulence factor.

TABLE 3

Pathogenesis of vMyx135KO Compared to Wildtype Controls

| | Observations and Time of onset (number + days indicates first appearance in days post injection) | | |
| --- | --- | --- | --- |
| Clinical Signs | Lausanne (4 animals) | vMyx135KO (6 animals) | vMyx135REV (3 animals) |
| inoculation site | 2 days: red, visible slightly raised 4 days: red, dark centre | 4 days: 11-16 mm red, raised, dark centre | 3 days: small red lump, slightly raised |
| satellites | 4 days | 6 days: just beginning, over course of infection very few observed | 6 days: 5-10 visible increasing to 30-40 satellites visible by day 8 |

TABLE 3-continued

Pathogenesis of vMyx135KO Compared to Wildtype Controls

Observations and Time of onset
(number + days indicates first appearance in days post injection)

| Clinical Signs | Lausanne (4 animals) | vMyx135KO (6 animals) | vMyx135REV (3 animals) |
|---|---|---|---|
| conjunctival inflammation | none observed | 9 days: single rabbit discharge from eye | none observed |
| anogenital edema | 7 days: swelling | 7 days: redness, swelling | |
| secondary lesions | 6-7 days: first around eyes then ears | 7 days: few small red spots not yet lesions, ears eyes | 6 days: first observed as red areas on eyelids, clearly lesion by day 7 |
| respiratory difficulty | little or none | little or none | little or none |
| lesion regression | | 11 days: 25 mm, black, scabby satellites losing colour and becoming scabby 13 days: scab beginning to separate from healthy tissue | |
| | two animals euthanized day 9 two animals euthanized day 10 | all animals recovered | three animals euthanized day 10 |

Figure 40:
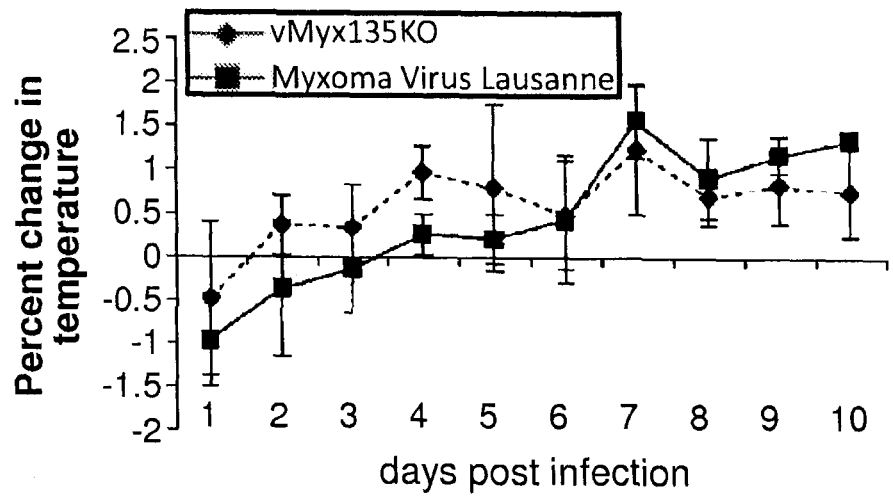
FIG. 40 is a graph of body temperature in rabbits infected with vMyxLau or vMyx135KO.

The temperature of rabbits was taken daily for the three days preceeding the study. This was considered the baseline body temperatures of the animals. We continued to take the temperatures daily of each animal for the duration of the study. However there was no difference in body temperature between the treatment groups (FIG. 40). This suggests that M135R does not play a role in the febrile response of infected animals.

M135R does not Bind or Inhibit Rabbit IFNα/β

Figure 41:
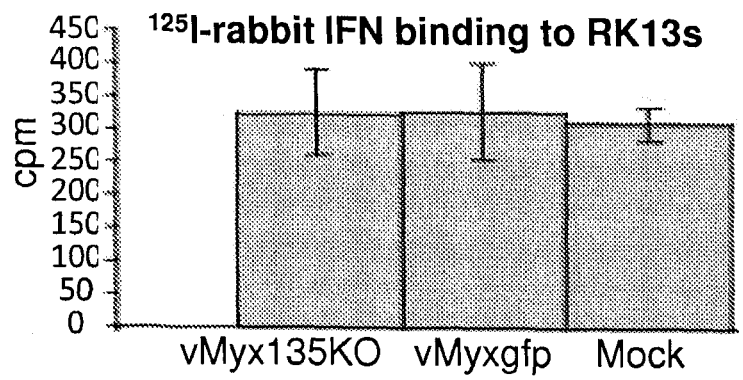
FIG. 41 is a graph of $^{125}$I emissions of cells mock infected or infected with vMyxgfp or vMyx135KO and treated with $^{125}$I-labelled rabbit interferon α/β.
Figure 41:
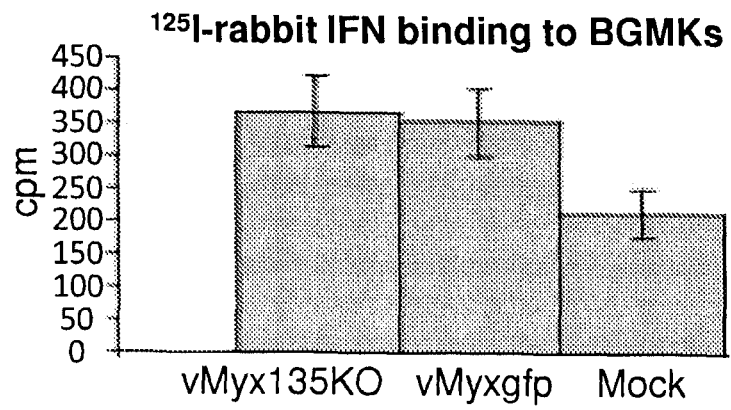
Figure 42:
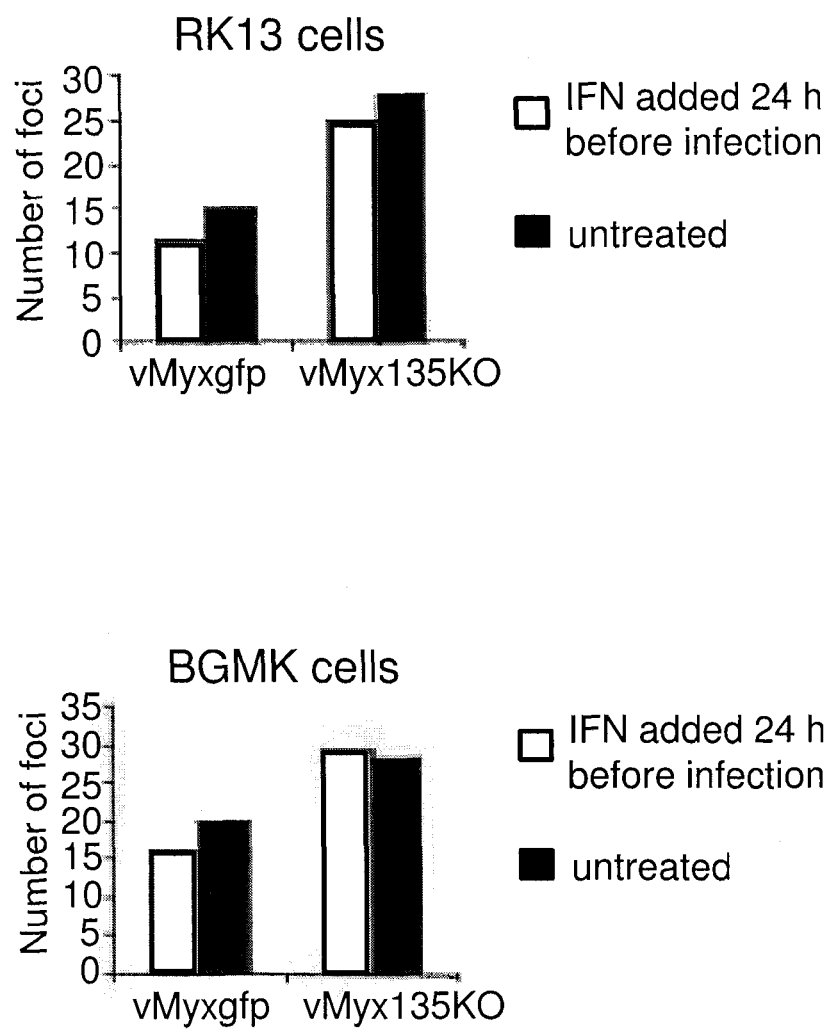
FIG. 42 is a graph of foci formed by infecting RK13 or BGMK cells with vMyxgfp or vMyx135KO, in which cells were untreated or treated with rabbit interferon α/β 24 hours prior to infection.

The sequence of M135R is similar to the vaccinia B18R, an IFNα/β receptor mimic. We tested the ability of M135R to bind rabbit type 1 IFN. We first iodinated rabbit IFN (5 μg, using Iodobeads) and tested the ability of vMyx135KO infected cells to bind $^{125}$I-rabbit IFN in comparison to cells infected with vMyxgfp (moi of 10). Cells were collected, washed and counted in a gamma counter. Deletion of M135R did not affect IFNα/β binding to infected cells and we did not observe any difference in the amount of IFN bound to the cell surface of either RK13 or BGMK cells (FIG. 41). As well, treatment of RK13 or BGMK cells with exogenous rabbit type1 IFN did not affect infection of cells by vMyx135KO (FIG. 42; cells were seeded in 12 well dishes and infected with the indicated virus at an moi of 0.01; fluorescent foci were counted 72-96 hours post infection; 200 units of rabbit IFNα/β was either added 24 hours prior to infection or cells were untreated). This same result was observed when cells were pretreated 24 h before infection to induce an anti-viral state in the cell. We did not notice any significant difference in the foci formed following infection in either RK13 or BGMK cells (data not shown). This phenomenon was also true if cells were treated with human IFNα/D (data not shown). As well, we were unable to observe any binding when Ac135ΔTM supernatants were applied to rabbit IFN α/β adhered to a BIAcore chip (data not shown).

Figure 43:
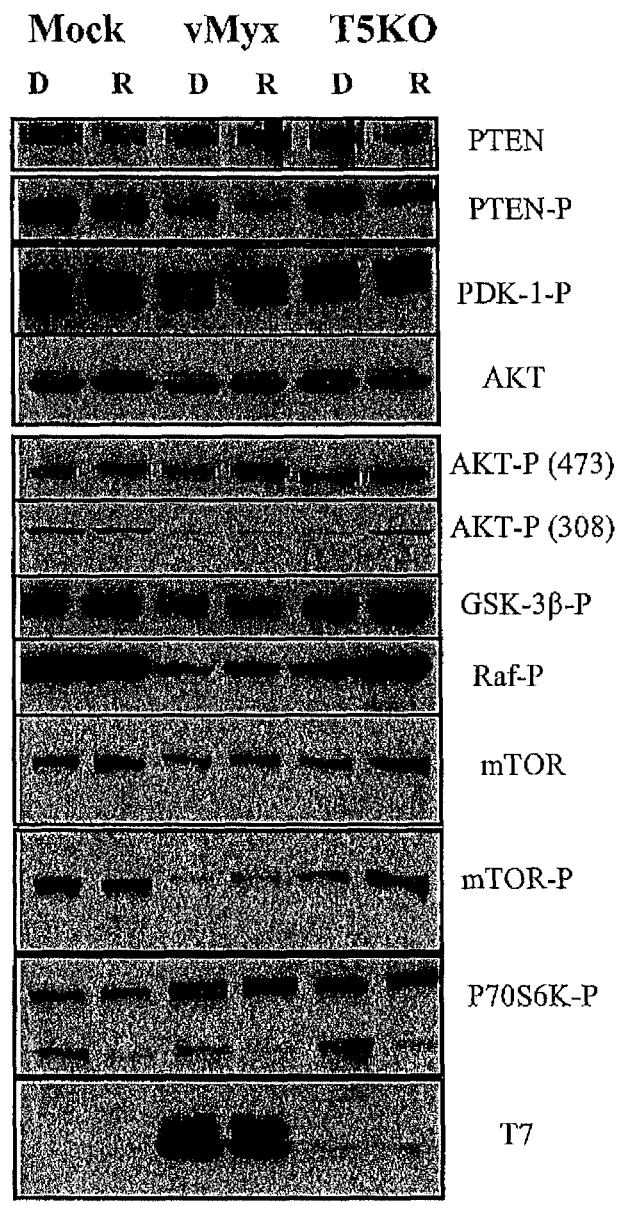
FIG. 43 is photographs of Western blots using cell lysates from 786-0 human cancer cells that were pre-treated with either 20 nM rapamycin (R) or with the vehicle control (D), probed using antibodies directed against the indicated proteins.

Example 3: Molecular Consequences of Inhibiting mTOR in the Context of Myxoma Virus Infection Western Blot analysis (FIG. 43) was performed using cell lysates from 786-0 cells, a Type II cancer cell line where rapamycin enhances myxoma virus infection. Lysates were collected 16 hours post infection with either vMyxLac or vMyxT5KO at an MOI of 3, or without virus infection. Indicated lanes contain protein from cells that were pre-treated with 20 nM rapamycin (designated R) or appropriate vehicle control (1:5000 dilution of DMSO, designated D) for 6 hours before infection. The blots were probed using primary antibodies directed against the indicated proteins.

As demonstrated, myxoma virus infection affects many of the signaling pathways that converge on mTOR, the physiologic target of rapamycin. In the context of infection with either wild type (vMyxLac) or MT-5 deficient (vMyxT5KO) virus, where rapamycin has a beneficial effect on virus replication, global effects are observed in many of these signaling molecules that would not be predictable based on treatment with rapamycin alone (see mock infected lanes). These effects include an increase in the kinase activity of AKT-1, Raf-1, GSK-3β and mTOR itself, as well as a decrease in the kinase activity of PTEN and p70S6K. This data indicate that these pathways are likely to play a role in myxoma virus permissiveness in human cancer cells lines.

As can be understood by one skilled in the art, many modifications to the exemplary embodiments described herein are possible. The invention, rather, is intended to encompass all such modification within its scope, as defined by the claims.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

All reference cited herein are fully incorporated by reference

What is claimed is:

1. A method for inhibiting a human cancer cell, comprising contacting a human cancer cell that is deficient in an innate antiviral response and permissive to Myxoma virus replication with an effective amount of a Myxoma virus that does not express functional M135R, wherein (i) part or all of the open reading frame that encodes M135R of the Myxoma virus is deleted, or (ii) part or all of the M135R gene regulatory region of the Myxoma virus is deleted wherein Myxoma virus inhibits human cancer cell; and wherein the human cancer cell is a glioma cell.

2. The method of claim 1, wherein the cancer cell exhibits abnormal interferon signaling.

3. The method of claim 1, wherein the Myxoma virus is genetically modified to express a therapeutic gene.

4. The method of claim 1, wherein the contacting step is performed by administering to a human cancer patient an effective amount of the Myxoma virus that does not express functional M135R; and wherein the human cancer patient has glioma.

5. The method of claim 4, wherein the Myxoma virus is genetically modified to express a therapeutic gene.

6. The method of claim 4, wherein the virus is administered to the site of the cancer in the cancer patient by injection.

7. The method of claim 4, wherein the virus is administered to the cancer patient systemically.

8. The method of claim 4, wherein the human cancer patient is further administered with rapamycin.

9. The method of claim 4, wherein the human cancer patient is further administered with an anti-cancer agent.

10. The method of claim 9, wherein the anti-cancer agent is a chemotherapy agent.

11. The method of claim 1, wherein part or all of the open reading frame that encodes M135R of the Myxoma virus is deleted.

12. The method of claim 1, wherein part or all of the M135R gene regulatory region of the Myxoma virus is deleted.

* * * * *

SEQUENCE LISTING

<160> NUMBER OF SEQ ID NOS: 2

<210> SEQ ID NO 1
<211> LENGTH: 178
<212> TYPE: PRT
<213> ORGANISM: Myxoma virus

<400> SEQUENCE: 1

Met Val Phe Ile Phe Ile Ile Thr Cys Val Cys Leu Val Thr Arg Ser
1               5                   10                  15

Cys Gly Gly Gly Leu Glu Asp Asp Ile Asp Arg Ile Phe Gln Lys Arg
            20                  25                  30

Tyr Asn Glu Leu Ser Gln Pro Ile Lys Arg Asn Met Arg Thr Leu Cys
        35                  40                  45

Lys Phe Arg Gly Ile Thr Ala Thr Met Phe Thr Glu Gly Glu Ser Tyr
    50                  55                  60

Leu Ile Gln Cys Pro Ile Ile His Asp Tyr Val Leu Arg Ala Leu Tyr
65                  70                  75                  80

Asp Leu Val Glu Gly Ser Tyr Thr Val Arg Trp Glu Arg Glu Thr Glu
                85                  90                  95

Asp Asp Val Glu Ser Val Asp Pro Lys Leu Val Lys Gly Thr Leu Leu
            100                 105                 110

Tyr Leu Gln Pro Asn Ala Ser Ser Ile Gly Thr Tyr Leu Cys Thr Leu
        115                 120                 125

His Asp Asn Arg Gly Met Cys Tyr Gln Ser Val Ala His Val Ile Arg
    130                 135                 140

Arg Pro Lys Met Gln Cys Val Lys His Ala His Thr Thr Ser Asp Ser
145                 150                 155                 160

Asn Leu Trp Ile Tyr Leu Ala Ile Leu Ala Val Leu Ile Ser Leu Gly
                165                 170                 175

Val Leu

<210> SEQ ID NO 2
<211> LENGTH: 179
<212> TYPE: PRT
<213> ORGANISM: Vaccinia virus

<400> SEQUENCE: 2

Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

-continued

```
Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His
```